(12) United States Patent
Barbut

(10) Patent No.: US 6,231,551 B1
(45) Date of Patent: May 15, 2001

(54) PARTIAL AORTIC OCCLUSION DEVICES AND METHODS FOR CEREBRAL PERFUSION AUGMENTATION

(75) Inventor: Denise Barbut, New York, NY (US)

(73) Assignee: Coaxia, Inc., Maple Grove, MN (US)

(*) Notice: Subject to any disclaimer, the term of this patent is extended or adjusted under 35 U.S.C. 154(b) by 0 days.

(21) Appl. No.: 09/260,371

(22) Filed: Mar. 1, 1999

(51) Int. Cl.$^7$ .................................................. A61M 5/315
(52) U.S. Cl. .................... 604/236; 604/96.01; 604/532; 606/198
(58) Field of Search ............................ 604/96, 101, 507, 604/102, 532, 236, 509, 96.01, 102.01; 606/194, 198, 200, 159

(56) References Cited

U.S. PATENT DOCUMENTS

| | | | |
|---|---|---|---|
| 4,601,706 | * | 7/1986 | Aillon . |
| 4,798,588 | * | 1/1989 | Aillon . |
| 5,330,451 | | 7/1994 | Gabbay . |
| 5,330,498 | | 7/1994 | Hill . |
| 5,334,142 | | 8/1994 | Paradis . |
| 5,437,633 | | 8/1995 | Manning . |
| 5,449,342 | | 9/1995 | Hirose et al. . |
| 5,458,574 | | 10/1995 | Machold et al. . |
| 5,599,329 | | 2/1997 | Gabbay . |
| 5,662,671 | * | 9/1997 | Barbut et al. .................... 606/200 |
| 5,678,570 | | 10/1997 | Manning . |
| 5,702,368 | | 12/1997 | Stevens et al. . |
| 5,711,754 | | 1/1998 | Miyata et al. . |
| 5,814,016 | | 9/1998 | Valley et al. . |
| 5,820,593 | | 10/1998 | Safar et al. . |
| 5,827,237 | | 10/1998 | Macoviak et al. . |
| 5,855,210 | | 1/1999 | Sterman et al. . |
| 6,010,522 | * | 1/2000 | Barbut et al. .................... 606/200 |

FOREIGN PATENT DOCUMENTS

WO99/30765  6/1999  (WO) .
WO99/58174  11/1999  (WO) .

OTHER PUBLICATIONS

Nussbaum et al., "Intra–Aortic Balloon Counterpulation Augments Cerebral Blood Flow in the Patient with Cerebral Vasospasm; a Xenon–Enhanced Computed Tomograph Study," *Neurosurgery*, 42(1):206–14 (1998).

Nussbaum et al., "Intra–Aortic Balloon Counterpulsation Augments Cerebral Blood Flow in a Canine Model of Subarachnoid Hemorrhage–Induced Cerebral Vasospasm," *Neurosurgery*, 36(4):879–86 (1995).

(List continued on next page.)

*Primary Examiner*—Anhtuan T. Nguyen
*Assistant Examiner*—Michael M Thompson
(74) *Attorney, Agent, or Firm*—Lyon & Lyon LLP

(57) ABSTRACT

Methods are provided for partial aortic occlusion for cerebral perfusion augmentation in patients suffering from global or focal cerebral ischemia. Alternatively, the methods can be used to partially occlude aortic blood flow to condition the spinal cord to secrete neuroprotective agents prior to abdominal aortic aneurysm repair. The methods can also be used to partially occlude the renal arteries to reduce renin secretion in hypertensive patients. Partial occlusion of a vessel can be accomplished by a device comprising an elongate catheter, a distally mounted expandable occluder, a variable flow mechanism, and a manometer. The occluder may comprise two conical shells or an inflatable ring-shaped balloon disposed about a cylindrical sleeve. Other medical devices, such as an atherectomy catheter, can be inserted distal the occluder to provide therapeutic intervention.

13 Claims, 20 Drawing Sheets

OTHER PUBLICATIONS

Tranmer et al., "Pulsatile Versus Nonpulsatile Blood Flow in the Treatment of Acute Cerebral Ischemia," *Neurosurgery*, 19(5):724–31 (1986).

Bhayana et al., "Effects of Intraaortic Balloon Pumping on Organ Perfusion in Cardiogenic Shock," *Journal of Surgical Research*, 26(2):108–113 (1979).

Nanas et al., "Counterpulsation: Historical Background, Technical Improvements, Hemodynamic and Metabolic Effects," *Cardiology*, 84:156–167 (1994).

Sabiston, *Textbook of Surgery*, Sabiston, Ed., W.B. Saunders Company, publisher, 1981, pp. 2462–2463.

Tranmer et al., "Intra–aortic balloon counterpulsation: a treatment for ishcaemic stroke?" *Neurol. Res.*, 11(2):109–113 (1989).

Cheung et al., Relationships Between Cerebral Blood Flow Velocities and Arterial Pressures During Intra–Aortic Counterpulsation:, *Journal of Cardiothoracic and Vascular Anesthesia*, 12:1, pp 51–57, Feb., 1998.

Apostolides et al., "Intra–aortic Balloon Pump Counterpulsation in the Management of Concomitant Cerebral Vasospasm and Cardiac Failure after Subarachnoid Hemorrhage: Technical Case Report", *Neurosurgery*, 38:5, May 1996, pp. 1056–1060.

Edmunds, Jr. et al., "An Adjustable Pulmonary Arterial Band", *Trans. Amer. Soc. Artificial Internal Organs*, vol. XVII, 1972, pp. 237–223.

* cited by examiner

PARTIAL AORTIC OCCLUSION DEVICES AND METHODS FOR CEREBRAL PERFUSION AUGMENTATION

FIELD OF THE INVENTION

The present invention relates generally to medical devices. More particularly, the invention relates to methods and devices for augmenting blood flow to a patient's vasculature. More particularly, the invention relates to apparatus and methods which provide partial obstruction ("coarctation") to aortic blood flow to augment cerebral perfusion in patients with global or focal ischemia. The devices and methods also provide mechanisms for continuous constriction and variable blood flow through the aorta.

BACKGROUND OF THE INVENTION

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. Shock is the state in which failure of the circulatory system to maintain adequate cellular perfusion results in reduction of oxygen and nutrients to tissues. Within minutes of circulatory failure, tissues become ischemic, particularly in the heart and brain.

The most common form of shock is cardiogenic shock, which results from severe depression of cardiac performance. The most frequent cause of cardiogenic shock is myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, acutely acquired ventricular septal defects, can also cause cardiogenic shock by reducing cardiac output. Additional causes of cardiogenic shock include cardiac arrhythmia, such as ventricular fibrillation.

Treatment of global cerebral ischemia involves treating the source of the systemic circulatory failure and ensuring adequate perfusion to the central nervous system. For example, treatment of cardiogenic shock due to prolonged cardiopulmonary bypass consists of cardiovascular support with the combination of inotropic agents such as dopamine, dobutamine, or amrinone and intra-aortic balloon counterpulsation. Vasoconstrictors, such as norepinephrine, are also administered systemically to maintain systolic blood pressure (at approximately above 80 mmHg). Unfortunately, these agents produce a pressure at the expense of flow, particularly blood flow to small vessels such as the renal arteries. The use of the vasoconstrictors is, therefore, associated with significant side effects, such as acute renal failure.

Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system and is the result of a disturbance of the cerebral circulation. Other causes of focal cerebral ischemia include vasospasm due to subarachnoid hemorrhage or iatrogenic intervention.

Traditionally, emergent management of acute ischemic stroke consists of mainly general supportive care, e.g. hydration, monitoring neurological status, blood pressure control, and/or anti-platelet or anti-coagulation therapy. Heparin has been administered to stroke patients with limited and inconsistent effectiveness. In some circumstances, the ischemia resolves itself over a period of time due to the fact that some thrombi get absorbed into the circulation, or fragment and travel distally over a period of a few days. In June 1996, the Food and Drug Administration approved the use of tissue plasminogen activator (t-PA) or Activase®, for treating acute stroke. However, treatment with systemic t-PA is associated with increased risk of intracerebral hemorrhage and other hemorrhagic complications. Aside from the administration of thrombolytic agents and heparin, there are no therapeutic options currently on the market for patients suffering from occlusion focal cerebral ischemia. Vasospasm may be partially responsive to vasodilating agents. The newly developing field of neurovascular surgery, which involves placing minimally invasive devices within the carotid arteries to physically remove the offending lesion may provide a therapeutic option for these patients in the future, although this kind of manipulation may lead to vasospasm itself.

In both global and focal ischemia, patients develop neurologic deficits due to the reduction in cerebral blood flow. Treatments should include measures to increase blood flow to the cerebral vasculature to maintain viability of neural tissue, thereby increasing the length of time available for interventional treatment and minimizing neurologic deficit while waiting for resolution of the ischemia. Augmenting blood flow to the cerebral vasculature is not only useful in treating cerebral ischemia, but may also be useful during interventional procedures, such as carotid angioplasty, stenting or endarterectomy, which might otherwise result in focal cerebral ischemia, and also cardiac procedures which may result in global cerebral ischemia, such as cardiac catheterization, electrophysiologic studies, and angioplasty.

New devices and methods are thus needed for augmentation of cerebral blood flow in treating patients with either global or focal ischemia caused by reduced perfusion, thereby minimizing neurologic deficits.

SUMMARY OF THE INVENTION

The invention provides vascular constriction devices and methods for augmenting blood flow to a patient's cerebral vasculature, including the carotid and vertebral arteries. The devices constructed according to the present invention comprise a constricting mechanism distally mounted on a catheter for delivery to a vessel, such as the aorta The constrictor is collapsed to facilitate insertion into and removal from the vessel, and expanded during use to restrict blood flow. When expanded, the constrictor has a maximum periphery that conforms to the inner wall of the vessel, thereby providing a sealed contact between it and the vessel wall. The constrictor typically has a blood conduit allowing blood flow from a location upstream to a location downstream. The devices further include a variable flow mechanism in operative association with the blood conduit, thereby allowing blood flow through the conduit to be adjusted and controlled. The devices can optionally include a manometer and/or pressure limiter to provide feedback to the variable flow mechanism for precise control of the upstream and downstream blood pressure. Other medical devices, such as an infusion, atherectomy, angioplasty, hypothermia catheters or devices (selective cerebral hypothermia with or without systemic hypothermia, and typically hypothermia will be combined with measures to increase perfusion to overcome the decreased cerebral blood flow caused by the hypothermia, such that hypothermia and coarctation are complimentary), or electrophysiologic study (EPS) catheter, can be introduced through the constrictor to insert in the vessel to provide therapeutic interventions at any site rostrally.

In a preferred embodiment, the expandable constrictor comprises an outer conical shell and an inner conical shell. Each shell has an apex and an open base to receive blood flow. One or a plurality of ports traverses the walls of the two conical shells. Blood flows through the open base and through the ports. The inner shell can be rotated relative to the outer shell so that the ports align or misalign with the ports in the outer shell to allow variable blood flow past the occluder, thereby providing adjustable and controlled flow. The inner shell is rotated by a rotating mechanism, e.g., a torque cable disposed within the elongate tube and coupled to the inner shell. The constrictor can be expanded by, e.g., a resilient pre-shaped ring, graduated rings, or a beveled lip formed at the base of the shell, and collapsed by, e.g., pull wires distally affixed to the occluder or a guide sheath.

In another embodiment, the outer conical shell includes a plurality of resilient flaps, which are pivotally affixed to the base or the apex and can be displaced to variably control blood flow through the conduit. The flaps can be displaced by a plurality of pull wires affixed to the flaps.

In still another embodiment, the constrictor comprises a first cylindrical balloon mounted to a distal end of the catheter, and a second toroidal balloon disposed about the cylindrical balloon. The chamber of the first balloon communicates with an inflation lumen. Blood flow occurs through the cylindrical balloon and through the center of the toroidal balloon. The toroidal balloon is expanded by inflation through a second and independent inflation lumen to reduce blood flow through the cylindrical balloon. In this manner, the first balloon provides an inflatable sleeve and the second toroidal balloon provides variable control of blood flow through the sleeve. Other embodiments include an expandable sleeve (not a balloon) surrounded by a toroidal balloon for adjustably constricting the flow of blood through the cylindrical sleeve.

In a preferred method, the occlusion devices described above are inserted into the descending aorta through an incision on a peripheral artery, such as the femoral, subclavian, axillary or radial artery, in a patient suffering from global or focal cerebral ischemia, during cardiac surgery (including any operation on the heart, with or without CPB), or during aortic surgery (during circulatory arrest, as for aortic arch surgery, repair of an abdominal aortic aneurysm, or thoracic aneurysm repair, to reduce perfusion and the amount of blood loss in the operating field). The devices can be introduced over a guide wire. With assistance of transesophageal echocardiography (TEE), transthoracic echocardiography (TTE), intravascular ultrasound (IVUS), aortic arch cutaneous ultrasound, or angiogram, the constrictor is positioned downstream from the takeoff of the brachiocephalic artery and upstream from the renal arteries. The constrictor is expanded to partially occlude blood flow in the aorta and maintained during systole, during diastole, or during systole and diastole. The constrictor preferably achieves continuous apposition to the wall of the vessel, resulting in fewer emboli dislodgment. The pressure limiter, connected to the rotary unit and the pressure monitor, prevents the upstream and downstream blood pressure from exceeding, respectively, a set maximum and minimum pressure differential.

Flow rates can be varied within one cardiac cycle (e.g., 80% during systole, 20% during diastole, or 70% during systole, 30% during diastole), and every few cycles or seconds (e.g., 80% for 6 cycles, 20% for 2 cycles, or 70% for 5 cycles, 10% for 1 cycle). In certain cases it may be preferred to cycle to cycle between lesser and greater occlusion so that the brain does not autoregulate. This ensures constant and continued increased cerebral perfusion. In this manner, blood in the descending aorta is diverted to the cerebral vasculature, thereby increasing cerebral perfusion and minimizing neurological deficits. By selectively increasing cerebral blood flow, the use of systemically administered vasoconstrictors or inotropic agents to treat shock may be reduced or eliminated.

In another method, in patients anticipating a major cardiothoracic surgery, such as abdominal aortic aneurysm repair, the device is introduced and deployed approximately 24 hours prior to surgery, thereby inducing mild artificial spinal ischemia. This induces endogenous neuroprotective agents to be released by the spinal cord and/or brain in response to the ischemia, thereby protecting the tissue from ischemic insult of surgery. This technique is known as "conditioning". The devices are inserted into the descending aorta. To induce spinal ischemia, the constrictor is positioned downstream from the takeoff of the brachiocephalic artery and upstream from the renal artery and expanded to partially occlude blood flow in the aorta, resulting in reduction of blood flow to the spinal cord. A similar technique may be employed to condition the brain to stimulate production of neuroprotective agents. To induce cerebral ischemia, the constrictor is positioned upstream from the takeoff of the innominate artery, or between the innominate artery and the left common carotid artery.

Prolonged hypertension often causes ischemic damage to the kidneys. In still another method, the partial occlusion devices are introduced peripherally and positioned in the renal arteries to reduce blood pressure to the renal vasculature, thereby minimizing damage to the kidneys that might otherwise result from hypertension.

It will be understood that there are many advantages in using the partial aortic occlusion devices and methods disclosed herein. For example, the devices can be used (1) to provide variable partial occlusion of a vessel; (2) to augment and maintain cerebral perfusion in patients suffering from global or focal ischemia; (3) to condition the brain or spinal cord to secrete neuroprotective agents prior to a major surgery which will necessitate reduced cerebral or spinal perfusion; (4) to prolong the therapeutic window in global or focal ischemia; (5) to accommodate other medical devices, such as an atherectomy catheter; (6) prophylactically by an interventional radiologist, neuroradiologist, or cardiologist in an angiogram or fluoroscopy suite; (7) for prevention of cerebral ischemia in patients undergoing procedures, such as coronary catheterization or surgery, where cardiac output might fall as a result of arrhythmia, myocardial infarction or failure; (8) to treat shock, thereby eliminating or reducing the use of systemic vasoconstrictors; and (8) to prevent renal damage in hypertensives.

DETAILED DESCRIPTION OF THE PREFERRED EMBODIMENTS

The devices and methods disclosed herein are most useful in treating patients suffering from global cerebral ischemia due to systemic circulatory failure, and focal cerebral ischemia due to thromboembolic occlusion of the cerebral vasculature. However, it will be understood that the devices and methods can be used in other medical conditions, such as hypertension and spinal cord conditioning.

Figure 1:
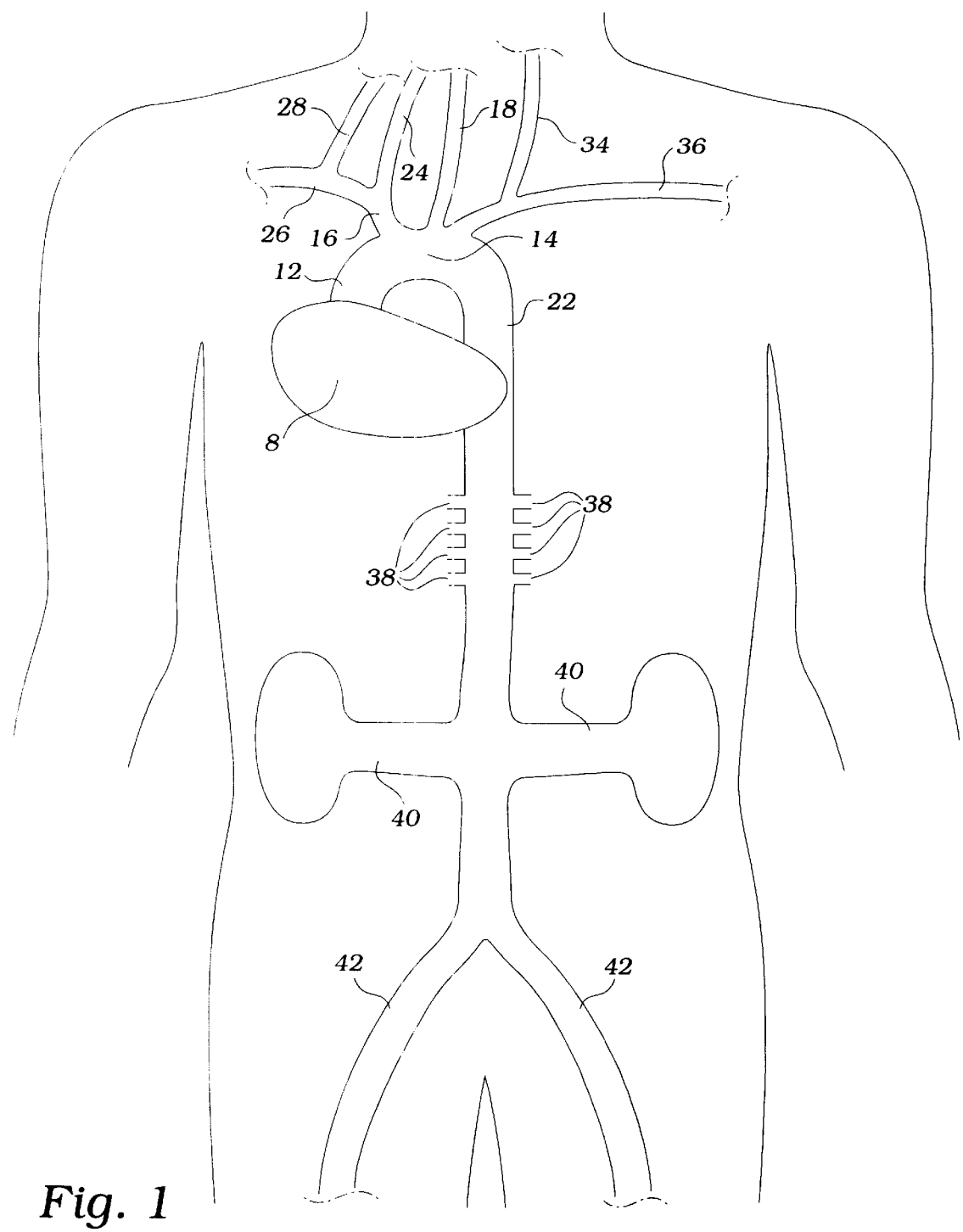
FIG. 1 illustrates a patient's systemic arterial circulation relevant to the present invention.

Systemic arterial circulation relevant to the methods of the present invention is described in FIG. 1. During systole, oxygenated blood leaving heart 8 enters aorta 10, which includes ascending aorta 12, aortic arch 14, and descending aorta 22. The aortic arch gives rise to brachiocephalic trunk 16, left common carotid artery 18, and left subclavian artery 20. The brachiocephalic trunk branches into right common carotid artery 24 and right subclavian artery 26. The right and left subclavian arteries, respectively, give rise to right vertebral artery 28 and left vertebral artery 34. The descending aorta gives rise to a multitude of arteries, including lumbar (i.e., spinal) arteries 38, which perfuse the spinal cord, renal arteries 40, which perfuse the kidneys, and femoral arteries 42, which perfuse the lower extremities.

Figure 2:
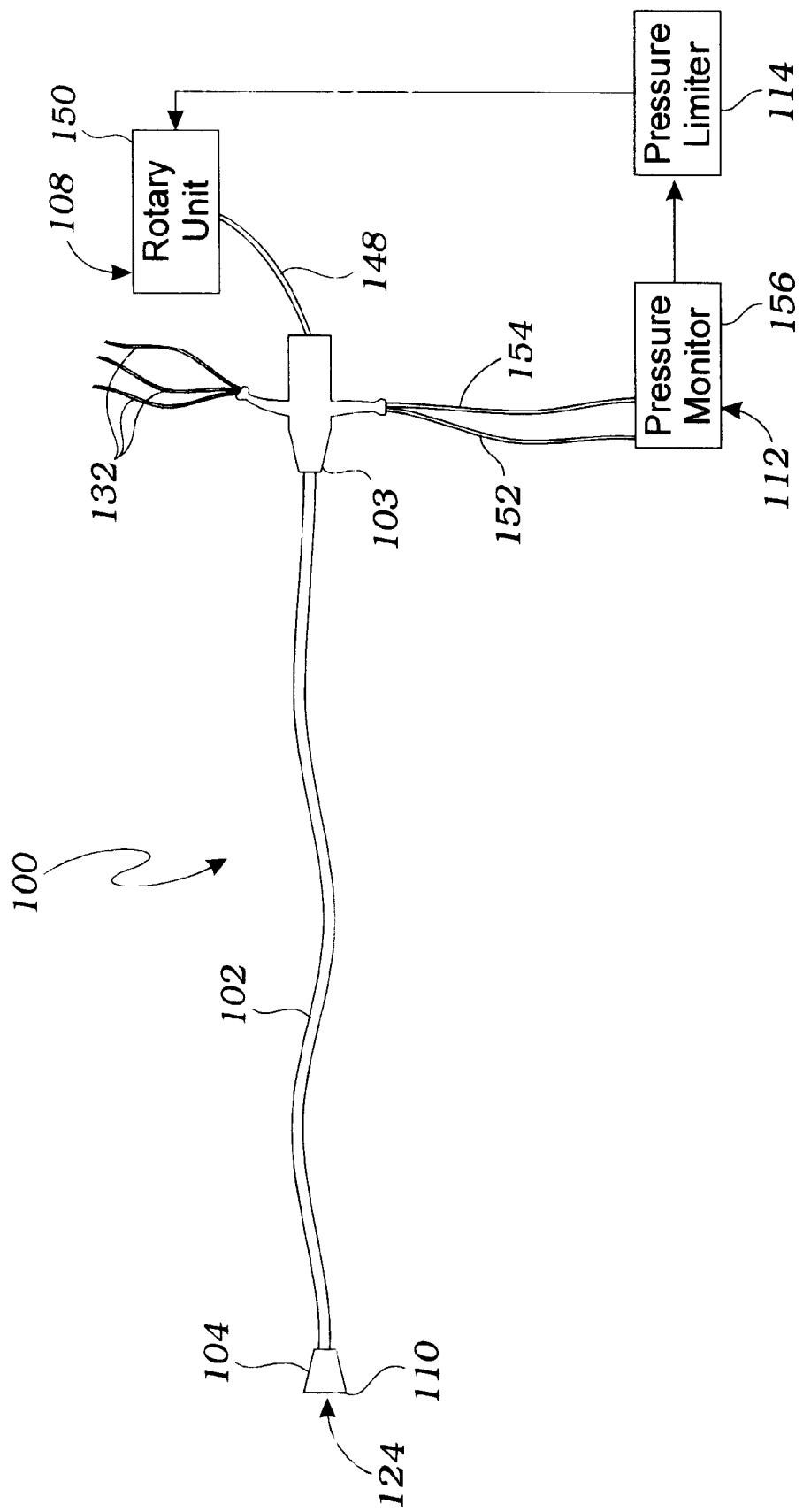
FIG. 2 illustrates an embodiment of the devices constructed according to the present invention for providing partial occlusion of a vessel.

FIG. 2 depicts occlusion catheter 100 for use in the methods described herein. The device includes elongate catheter 102, distally mounted expandable constrictor, i.e., occluder, 104 having distal opening 124 and variable flow mechanism 108. The constrictor, when expanded, has maximum periphery 110, which conforms to the inner wall of a vessel to form a secure seal with the vascular wall, such that blood flow through the vessel can be effectively controlled. Opening 124 receives blood from distal the constrictor and controls the passage of blood proximal the constrictor. Variable flow mechanism 108, connected to rotary unit 150, operates the constrictor, thereby controlling (1) the flow rate through the occlusion, and (2) upstream blood pressure. Preferably, the device includes manometer 112, which is connected to pressure monitor 156 and pressure limiter 114. Rotary unit 150 receives blood pressure measurements from the manometer. Pressure limiter 114, connected to the rotary unit and the pressure monitor, prevents the upstream and downstream blood pressure from exceeding, respectively, a set maximum and minimum pressure differential. A proximal end of the catheter is equipped with adapter 103, from which pull wires 132 can be manipulated for collapsing the occluder and to which the rotary unit, pressure monitor, and/or pressure limiter can be connected.

Figure 3:
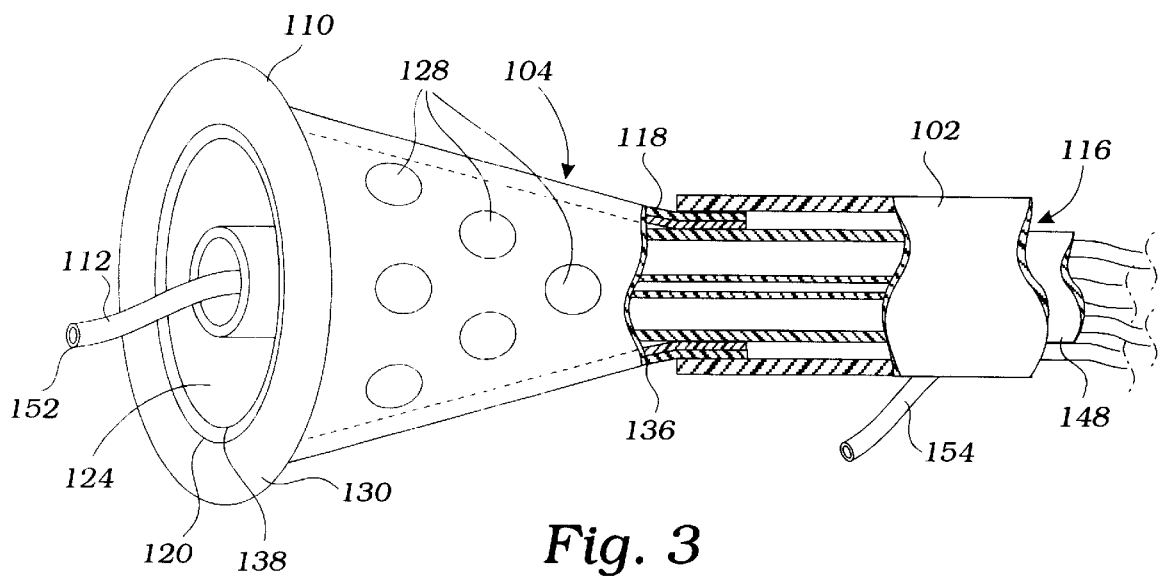
FIG. 3 illustrates a constrictor of the device depicted in FIG. 2.

Referring to FIG. 3, the occlusion device comprises catheter 102 and constrictor 104. The catheter is constructed from a biocompatible and flexible material, e.g., polyurethane, polyvinyl chloride, polyethylene, nylon, etc. The catheter includes lumen 116 through which various operative elements pass. Alternatively, the catheter may include more than one lumen to support various operative elements. The catheter also includes proximal adapter 103 (see FIG. 2), which provides an interface between the catheter and the various instruments received by the catheter. The occluding mechanism consists of outer conical shell 118 and inner conical shell 136, each having a distal open base and a proximal apex. Pre-shaped ring 130 is affixed to base 120 of the outer shell to facilitate expansion of the constrictor. The ring is formed of a resilient material, capable of expanding the occluder to achieve a maximum periphery, which is defined by the outer circumference of the ring. Ring 130, may, in certain embodiments, further include an anchoring mechanism, such as hooks, bonded to the outer circumference of the ring. Expansion of the ring causes the grasping structure to engage the surface of the vessel wall, thereby securing the occluder and preventing displacement in the vessel due to force exerted by blood flow. In other embodiments, the anchoring is provided by an adhesive strip, vacuum, or merely by frictional engagement of the vessel lumen by the ring.

The constrictor can be collapsed to facilitate insertion into and removal from a vessel. A plurality of pull wires 132 (FIG. 2) are disposed within torque cable 148, and are distally connected to base 120 of outer shell 118 and proximally passes through adapter 103. The constrictor is collapsed by applying a tensile force on wires 132, using torque cable 148 to provide leverage to the pull wires, thereby drawing the circumference of the open base 120 towards its center and collapsing the occluder. A guide sheath (not shown) can be alternatively used to collapse the constrictor. Using this technique, the guide sheath would cover the constrictor and be withdrawn to release the constrictor and advanced to collapse the constrictor.

Figure 8:
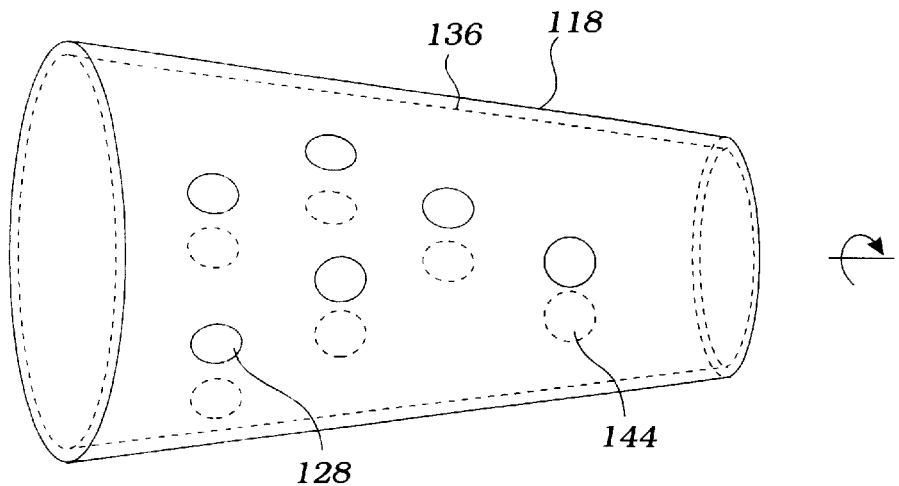
FIG. 8 illustrates complete misalignment of the ports on the outer and inner conical shells.
Figure 9:
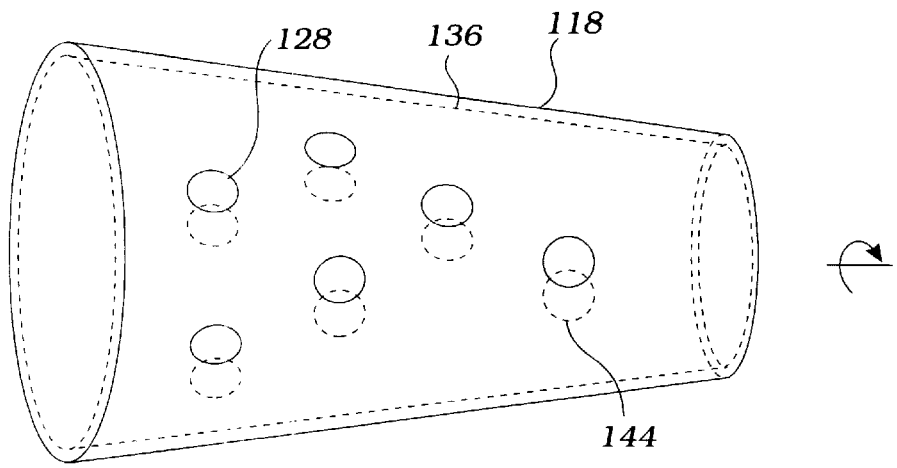
FIG. 9 illustrates partial alignment of the ports on the outer and inner conical shells.
Figure 10:
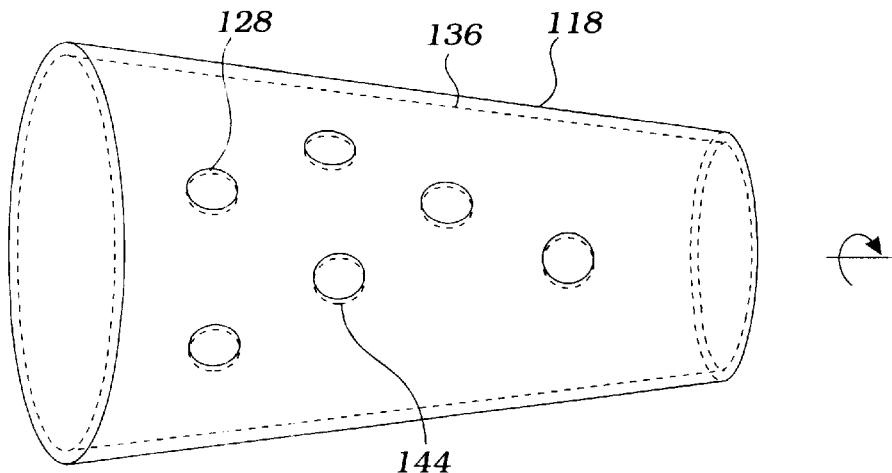
FIG. 10 illustrates complete alignment of the ports on the outer and inner conical shells.

Opening 124 is formed in base 138 and 120 of the respective inner and outer conical shells to provide an inlet for blood flow. Conical interior 106 communicates with ports 128 of the outer shell. When the constrictor is deployed, blood flows into opening 124, through interior 106, and exits through ports 128. The occluding mechanism comprises inner conical shell 136 (partially shown in phantom in FIG. 3), which is rotatably disposed within outer shell 118 as shown in FIGS. 8, 9, and 10. The inner shell can be rotated relative to the outer shell through torque cable 148, which is disposed in lumen 116 of catheter 102.

Manometer 112 comprises upstream pressure tube 152 and downstream pressure tube 154, both connected proximally to a pressure monitor to provide respective blood pressure measurements upstream and downstream the constrictor. The upstream pressure tube extends distal to opening 124, or may be attached to the inner shell. The downstream pressure tube extends through an orifice in the catheter proximal to the constrictor. The upstream and downstream blood pressure measurements are recorded and displayed by the pressure monitor at a proximal end of the catheter. A pressure limiter, programmed with a maximum pressure threshold to limit the upstream blood pressure and a minimum pressure threshold to limit the downstream blood pressure, is connected to the pressure monitor to receive pressure measurements therefrom, and transmits information to a rotary unit. The limiter thereby prevents the rotary unit from rotating the inner shell relative to the outer shell in a manner that would cause the upstream blood pressure to exceed the maximum threshold, or the downstream blood pressure to fall below the minimum threshold. Without the rotary unit, torque cable 148 can also be manually rotated to obtain desired upstream and downstream blood pressures. An audible alarm may be incorporated into the pressure limiter to sound when blood pressures exceeds the thresholds. The pressure limiter may further comprise an interlocking device. The interlocking device, in operative association with upstream and downstream tubes 152 and 154, can lock inner shell 136 with respect to outer shell 118 as blood pressures approach the set thresholds. It should be noted that although the rotary unit, pressure monitor, and pressure limiter are shown as separate units, they may be incorporated into an integral unit.

Figure 4A:
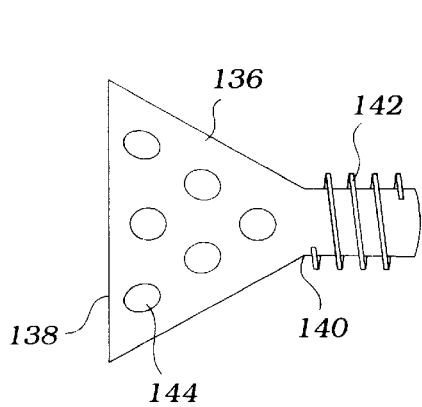
FIG. 4A illustrates an outer conical shell employed in the constrictor of FIG. 3.
Figure 4B:
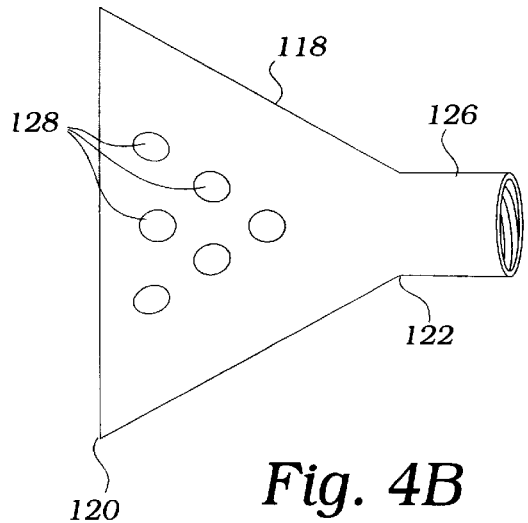
FIG. 4B illustrates an inner conical shell employed in the constrictor of FIG. 3.

Referring to FIGS. 4A and 4B, the expanded constrictor comprises outer conical shell 118 having base 120 and apex 122, and inner conical shell 136 having base 138 and apex 140. The constrictor is preferably composed of a biocompatible material coated with heparin to prevent blood clotting. The conical shape of the expanded constrictor minimizes turbulence caused by placement of the occluder in the vessel. The outer and inner shells include 2, 3, 4, 5, 6, or any other number of ports 128 and 144, respectively, in communication with the conical interior to permit blood flow through the occluder. The inner shell can be rotated relative to the outer shell, so that ports 144 communicate with ports 128. Apices 122 and 140 of the respective outer and inner shells further comprise collar 126 and 142. The collars may include engaging threads, so that collar 142 can be inserted and secured into collar 126, and bonded to a distal end of the torque cable, such that the inner shell is coupled to and rotates with the torque cable. A rotary unit, preferably including a stepper motor (not shown), may be mechanically coupled to a proximal end of the torque cable to provide precise rotational position of the inner shell relative to the outer shell, thereby providing variable flow through the occluder.

Figure 5:
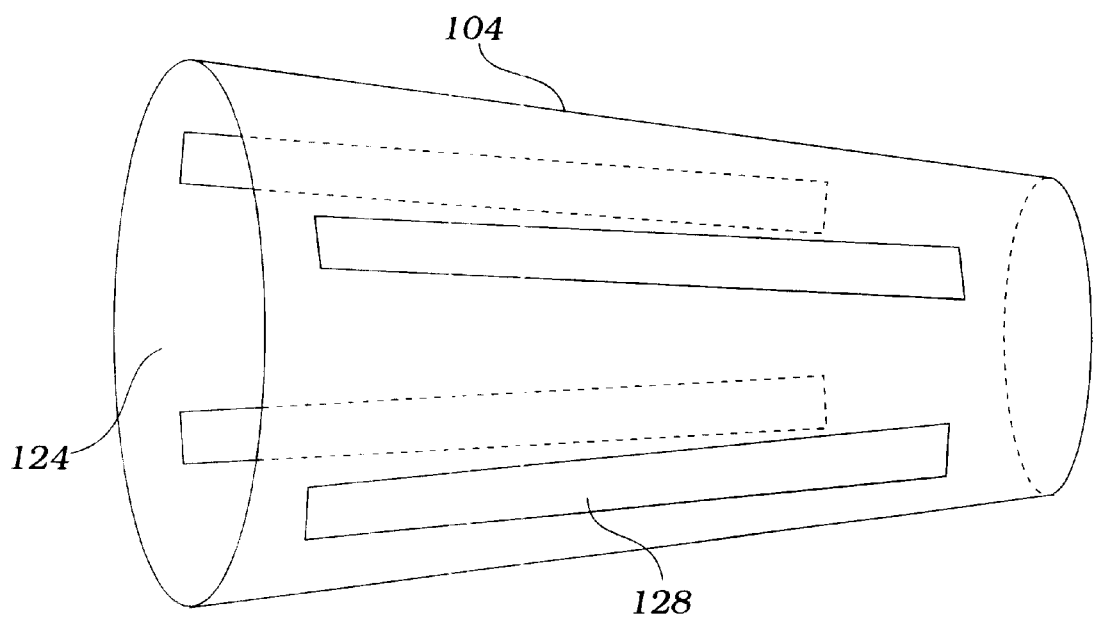
FIG. 5 illustrates an alternative embodiment of the constrictors of FIG. 3 having elongate rectangular ports.

Instead of having the circular ports in the inner and outer shells as depicted in FIGS. 4A and 4B, the constrictor may include 2, 3, 4, 5, 6, or any other number of ports having other suitable geometric shapes. FIG. 5 depicts constrictor 104 having a plurality of ports constructed as elongate rectangular slots 175.

Figure 6:
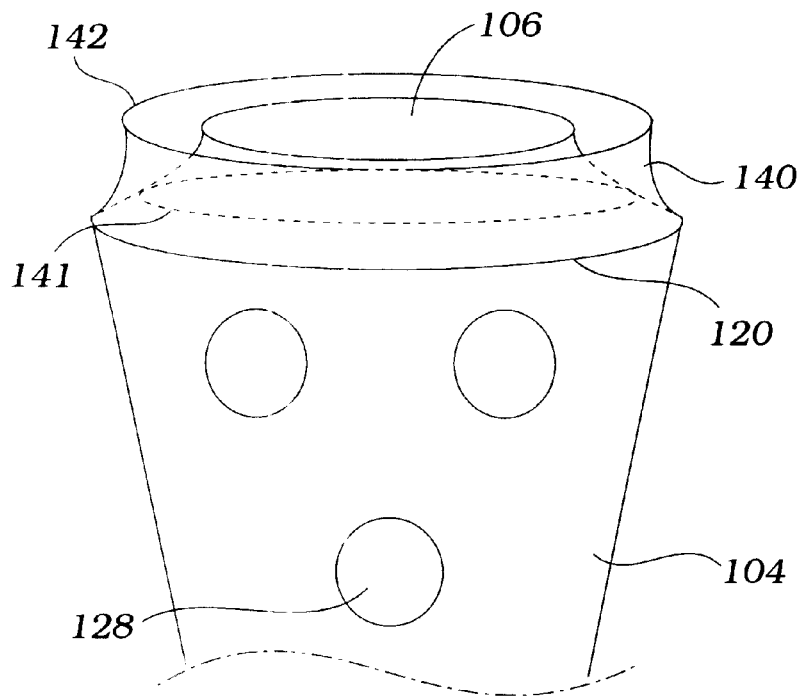
FIG. 6 illustrates another embodiment of the occluder having a beveled lip.

FIG. 6 depicts another embodiment of the constrictor, which comprises beveled lip 140 having distal end 142 and proximal end 141. The proximal end is affixed to base 120 of the outer conical shell. The proximal end has a larger diameter than the distal end and is everted to prevent the constrictor from being displaced in the direction of blood flow, thereby securing the constrictor in the vessel.

Figure 7:
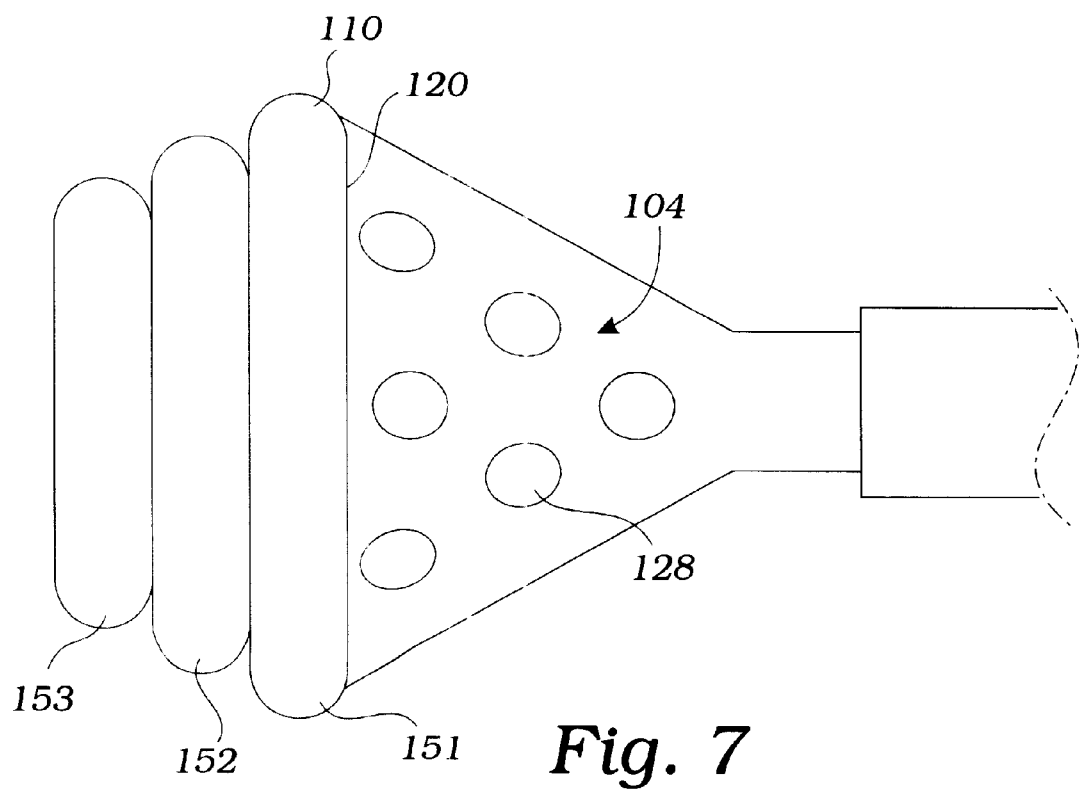
FIG. 7 illustrates another embodiment of the occluder having a plurality of graduated rings.

Still another embodiment of the occluder may includes 1, 2, 3, 4, 5, or any other number of graduated inflatable rings. In FIG. 7, ring 151 is affixed to the base of the conical shell. Ring 153, having the smallest inflated diameter, is attached to ring 152, which is then attached to ring 151, having the largest inflatable diameter. The fully inflated rings will have a thickness of approximately 2 to 3 millimeters. Similar to the beveled lip of FIG. 8, the rings prevent the outer conical shell from being displaced in the direction of blood flow, thereby securing the constrictor in the vessel.

The flow rate of blood through the constrictor can be easily controlled by rotating inner conical shell 136 (shown with dotted lines) relative to outer conical shell 118 as depicted in FIGS. 8, 9, and 10. In FIG. 8, the inner shell is rotated so that ports 144 and 128 are completely misaligned, thereby achieving no flow through the ports and complete vascular occlusion distally. As the inner shell is rotated clockwise relative to the second shell in FIG. 9, ports 144 on the inner shell become partially aligned with ports 128 on the outer shell, thereby achieving partial flow through the ports and partial vascular occlusion. In FIG. 10, with continuing clockwise rotation of the inner shell, ports 144 become completely aligned with ports 128, thereby achieving maximum flow through the ports. To provide a broader and more predictable range of blood flow through the conduit, the ports of the inner and outer shells are preferably of equal size and number such that they may align with each other.

Figure 11:
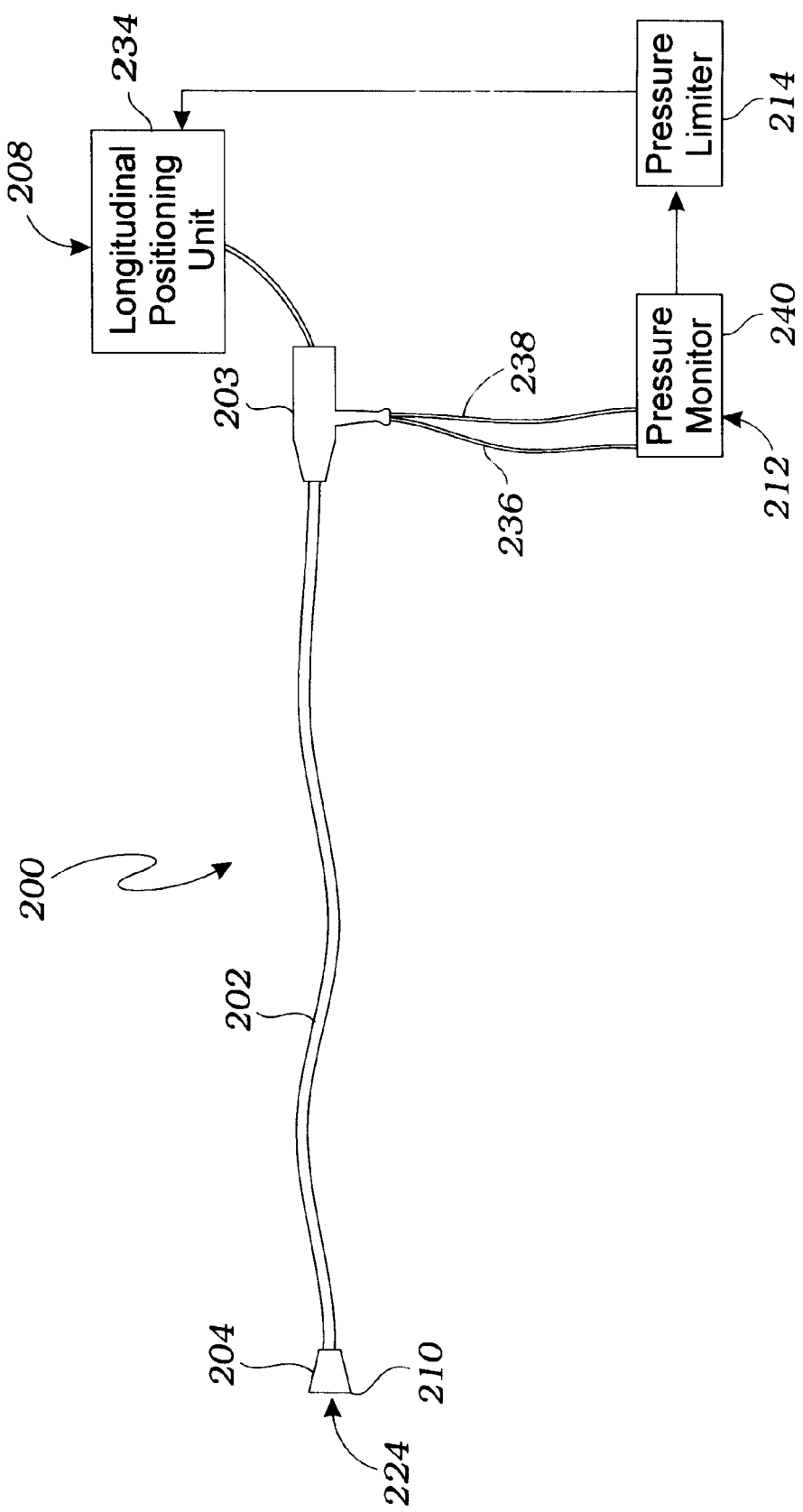
FIG. 11 illustrates another embodiment of the device for providing partial occlusion of a vessel.

FIG. 11 depicts another embodiment of the occlusion device for partial occlusion of blood flow in a vessel. Device 200 comprises elongate catheter 202, distally mounted expandable constrictor 204 with maximum periphery 210, opening 224, and variable flow mechanism 208 operatively associated with the constrictor. The catheter includes adapter 203 at its proximal end. Preferably, the device includes manometer 212 and pressure limiter 214, and pressure monitor 240. The pressure monitor records and displays blood pressure data received from the manometer. Longitudinal positioning unit 208, receiving signals from pressure limiter 214, and controls variable flow mechanism 208 to provide variable blood flow through the constrictor.

Figure 12:
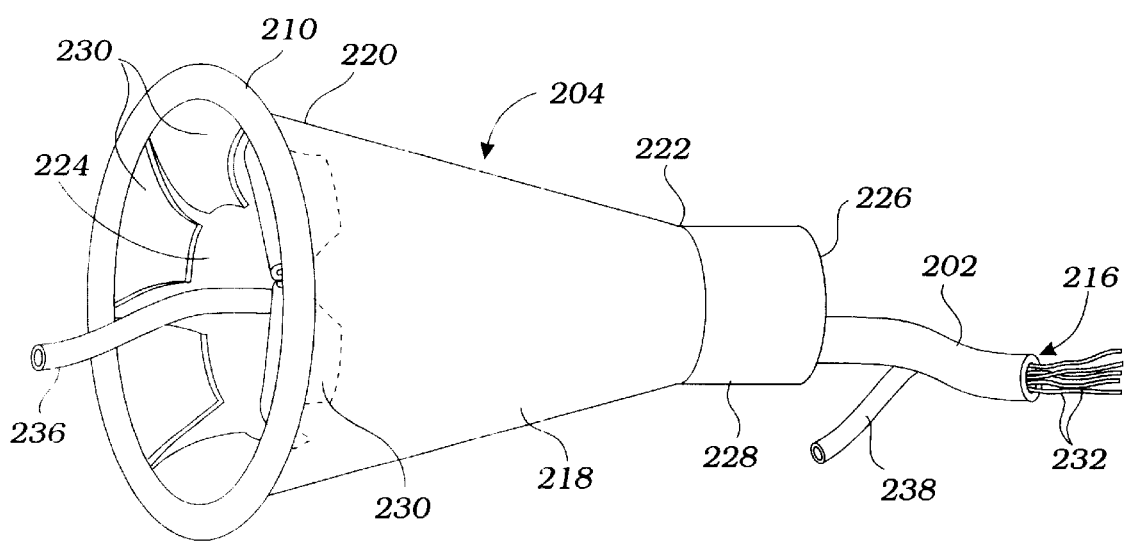
FIG. 12 illustrates another embodiment of the constrictor employed in the device of FIG. 11.

Referring to FIG. 12, catheter 202 includes lumen 216. Constrictor 204 comprises hollow conical shell 218 having base 220 and apex 222. The inner circumference of the base forms opening 224, which provides a distal inlet for blood flow through the constrictor. The inner circumference of apex 222 forms collar 228 with proximal opening 226, which provide an outlet for blood flow through the constrictor. The conical interior, disposed within shell 218, communicates with opening 224 distally and opening 226 proximally. When the base of the constrictor is positioned upstream in a vessel, blood flows into opening 224, through the conical interior, and exits downstream through opening 226. The catheter is bonded to collar 228 about a portion of its inner circumference. The constrictor is expanded by operation of ring 230, a beveled lip, or a series of graduated toroidal balloons as described above. The constrictor is collapsed and may be delivered to a vessel location by using a guide sheath.

The manometer comprises upstream pressure tube 236 and downstream pressure tube 238, which are disposed in lumen 216 of the catheter and connected proximally to a pressure monitor. The upstream pressure tube extends distal from the constrictor or may be bonded to the inner surface of the conical shell, thereby providing upstream blood pressure measurement. The downstream pressure tube extends through an orifice in the catheter proximal to the constrictor, thereby providing downstream blood pressure measurement.

The variable flow mechanism comprises a plurality of flaps 230 pivotally affixed to base 220. The flaps are preferably made of a resilient material, such as Nitinol, to resist movement caused by blood flow through the conduit. A plurality of pull wires 232, disposed through lumen 216, are distally connected to flaps 230, such that applying a tensile force to the wires pivotally displaces flaps 230 from their preformed position. Three of the flaps (shown in dotted lines) are displaced inward. Releasing the wires allows the resilient flaps to relax and return to their preformed position. The pull wires are coupled proximally to the longitudinal positioning unit, which provides precise displacement of the flaps relative to opening 224. Alternatively, wires 232 can be manually tensed to operate the flaps. The pressure limiter receives pressure measurements from the pressure monitor and transmits signals to the longitudinal positioning unit to prevent the upstream and downstream blood pressures from exceeding the set thresholds.

Figure 13A:
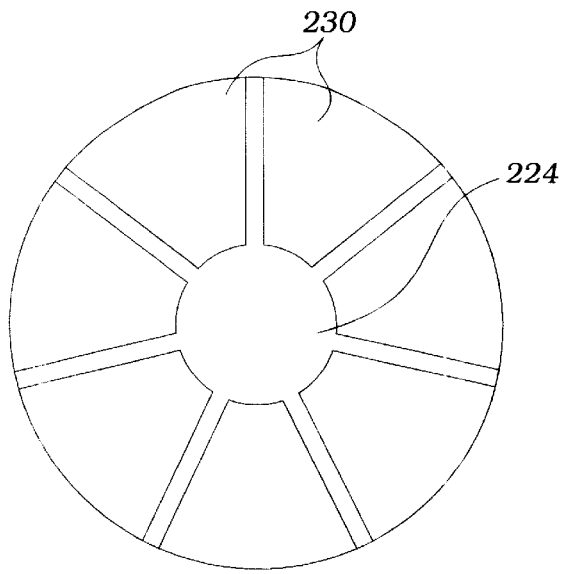
FIG. 13A illustrates a frontal view of the constrictor of FIG. 12 having a plurality of preformed flaps extending perpendicular to the longitudinal axis of the constrictor.
Figure 13C:
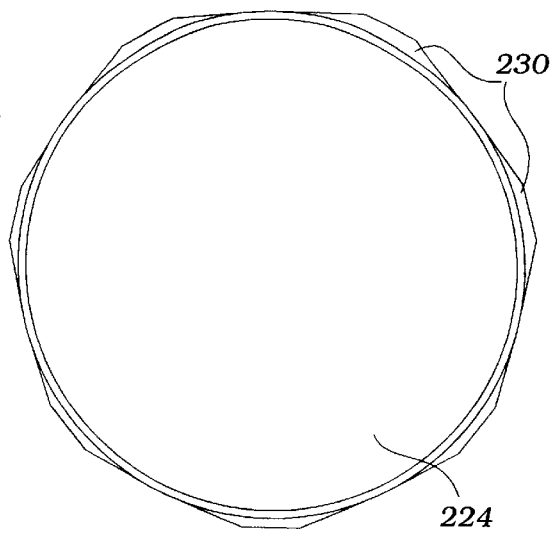
FIG. 13C illustrates a frontal view of the constrictor of FIG. 12 having a plurality of preformed flaps extending parallel to the longitudinal axis of the constrictor.
Figure 13B:
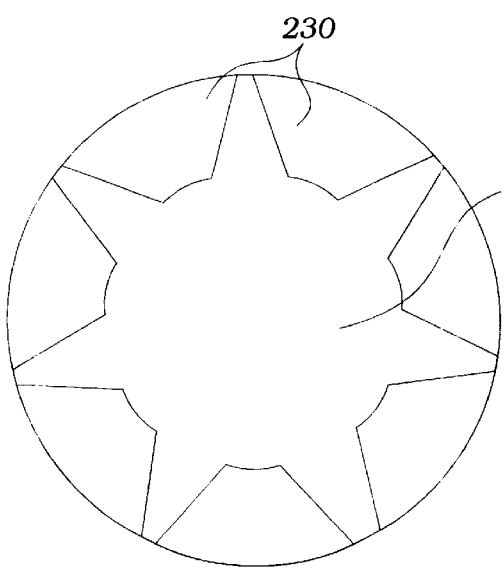
FIG. 13B illustrates a frontal view of the flaps of FIG. 13A under an external force.

FIGS. 13A, 13B, 13C, and 13D depict frontal views of the constrictor having flaps in various positions for controlling blood flow. In FIG. 13A, preformed flaps 230 extend radially inward toward the longitudinal axis of the catheter, as in the absence of a displacing force, i.e., an external force other than that created by blood flow. When the constrictor is positioned in the descending aorta, for example, the size of opening 224 and blood flow through the opening is minimized, thereby providing maximal aortic occlusion. In the presence of a displacing force, such as pulling the wires to displace flaps 230 from their preformed position as depicted in FIG. 13B, the size of aperture 224 and blood flow through the conduit increases, thereby providing partial aortic occlusion.

Figure 13D:
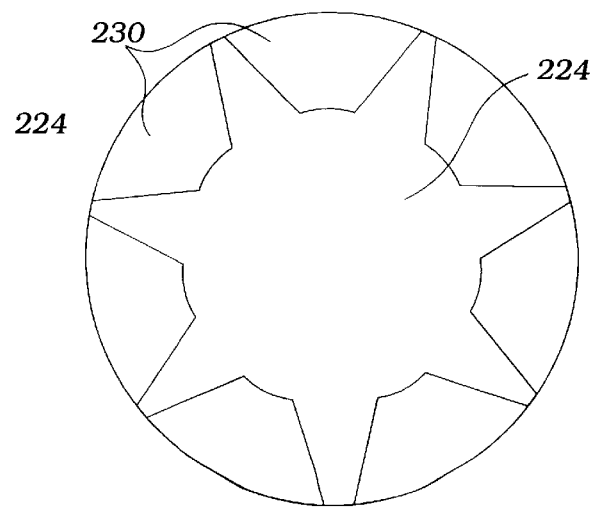
FIG. 13D illustrates a frontal view of the flaps of FIG. 13C under an external force.

Alternatively, preformed flaps 230 extend parallel to the longitudinal axis of opening 224 in the absence of a displacing force as depicted in FIG. 13C. The size of opening 224 and blood flow through the conduit are maximized, thereby providing minimal blood flow occlusion. In the presence of a displacing force, flaps 230 are pivotally displaced from their preformed position as depicted in FIG. 13D. The size of opening 224 and blood flow through the opening are minimized, thereby providing maximal blood flow occlusion. Thus, by pivotally displacing flaps 230 relative to opening 224, the size of the opening and flow rate through the constrictor is controlled to provide variable vessel occlusion.

The constrictor shown in FIG. 12 can be alternatively mounted on catheter 202, such that base 220 is proximal to apex 222 as shown in FIG. 14A. In this embodiment, flaps 230 are formed on open apex 222. When constrictor 204 is inserted downstream in the aorta, for example, pressure tube 238 extends distally from opening 226 to provide downstream blood pressure measurements, whereas pressure tube 236 extends proximally through an orifice in the catheter to provide upstream blood pressure measurements.

Figure 15:
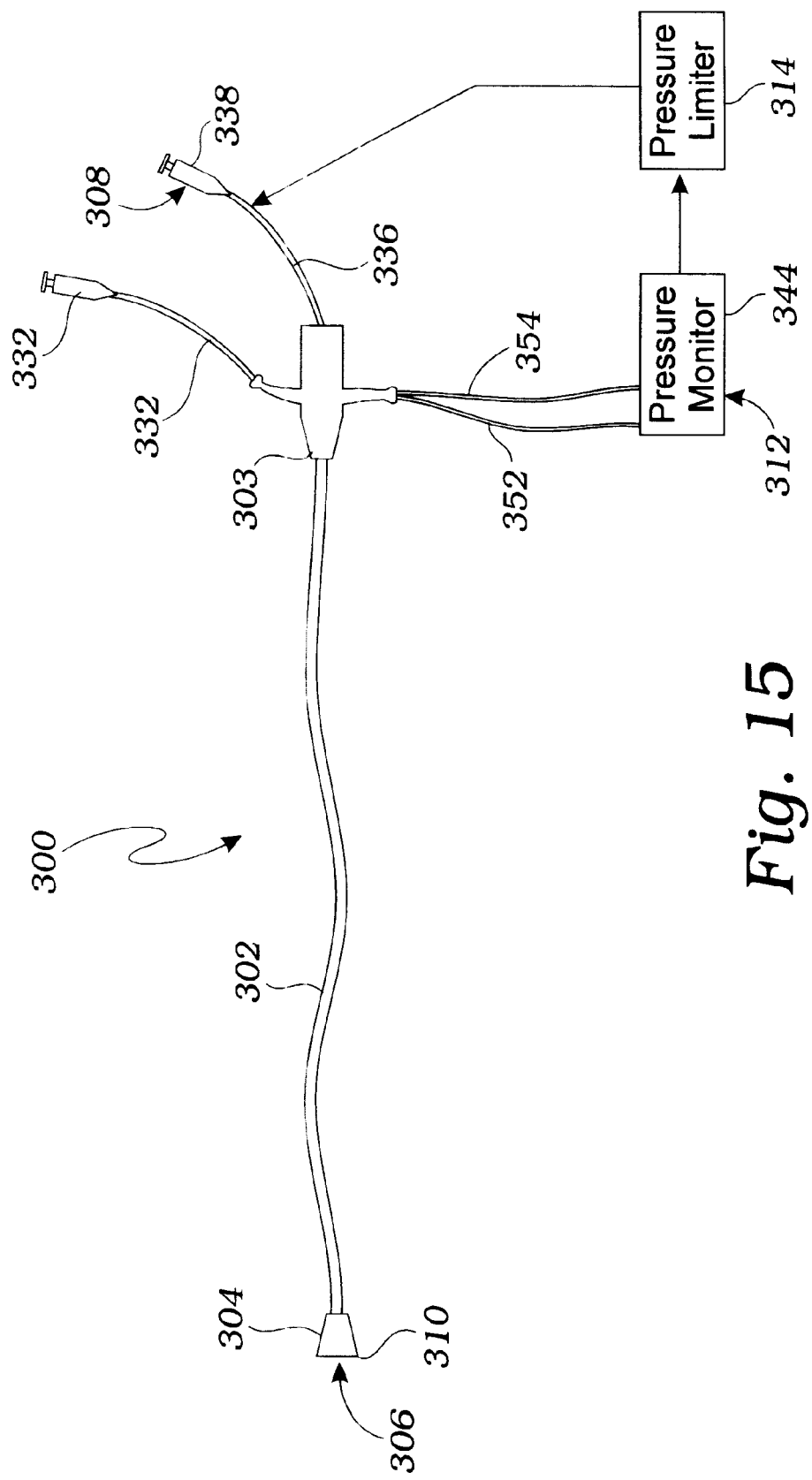
FIG. 15 illustrates still another embodiment of the device for providing partial occlusion of a vessel.

In FIG. 15, another embodiment of the device comprises catheter 302, a distally mounted occluder 304 with maximum periphery 310, blood passage 306 disposed within the constrictor, and variable flow mechanism 308 in operative association with the blood conduit. Inflation device 334 communicates with the constrictor, and inflation device 338 communicates with the variable flow mechanism. The device preferably includes proximal adapter 303, manometer 312, and pressure limiter 314. Pressure monitor 312 records and displays blood pressure data from the manometer. The pressure limiter is connected to the pressure monitor and to an interlocking valve on inflation device 338, such that the blood pressure upstream and downstream the constrictor can be controlled to prevent from exceeding set thresholds.

Figure 16:
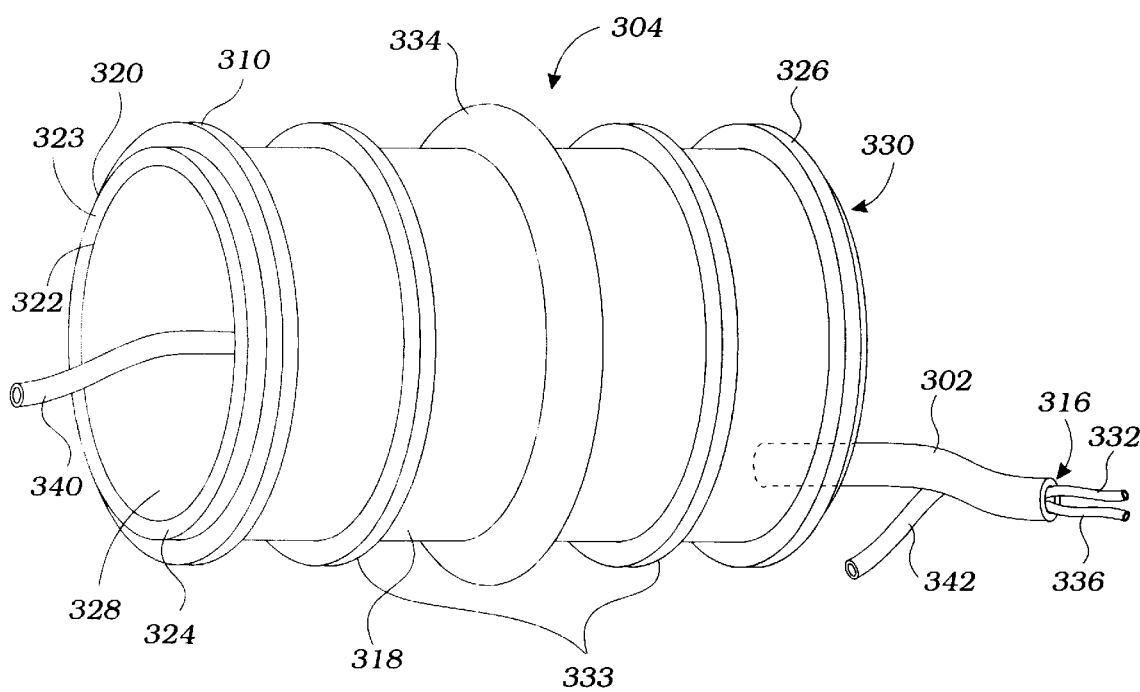
FIG. 16 illustrates an embodiment of the constrictor employed in the device of FIG. 15.

Referring to FIG. 16, constrictor 304 is mounted to a distal end of catheter 302 having lumen 316. The constrictor comprises a sleeve or cylindrical balloon 318 having outer wall 320 and inner wall 322, which enclose chamber 323. The cylindrical balloon has first end 324 with opening 328 and second end 326 with opening 330. Catheter 302 is bonded to inner wall 322 of the cylindrical balloon. Inflation tube 332, housed within lumen 316 of the catheter, communicates distally with the cylindrical balloon and proximally with a syringe or other inflation device. The cylindrical balloon can be expanded or collapsed by injecting or removing air, saline, or other medium. Occlusion is provided by toroidal balloon 334 disposed about the outer or inner surface of sleeve 318 and communicating with inflation tube 336 and a syringe. The inflation device may include an interlocking valve to prevent unintended deflation.

Lumen 306 communicates with opening 328 distally and opening 328 proximally. When deployed in a vessel, blood flows through lumen 306 and exits downstream opening 330. The constrictor may further include an anchoring structure, shown in FIG. 16 as rings 333, which are disposed about outer wall 320 of the cylindrical sleeve and define maximum periphery 310 of the occluder.

Manometer 312 comprises upstream pressure tube 340 and downstream pressure tube 342, which are operatively connected proximally to a pressure monitor. Pressure tube 340 is bonded to the lumen of the cylindrical balloon and extends distal to provide upstream blood pressure measurements, while tube 342 emerges from the catheter proximal the occluder to provide downstream blood pressure measurements.

Figure 17:
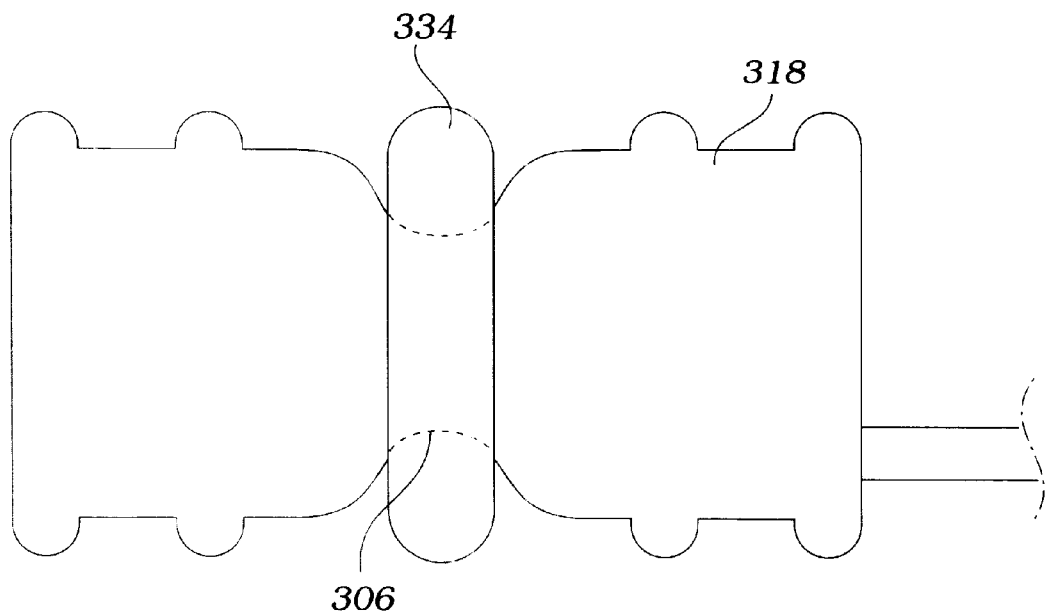
FIG. 17 illustrates the constrictor of FIG. 16, having an inflated ring-shaped balloon for reducing blood flow through a blood conduit.
Figure 18:
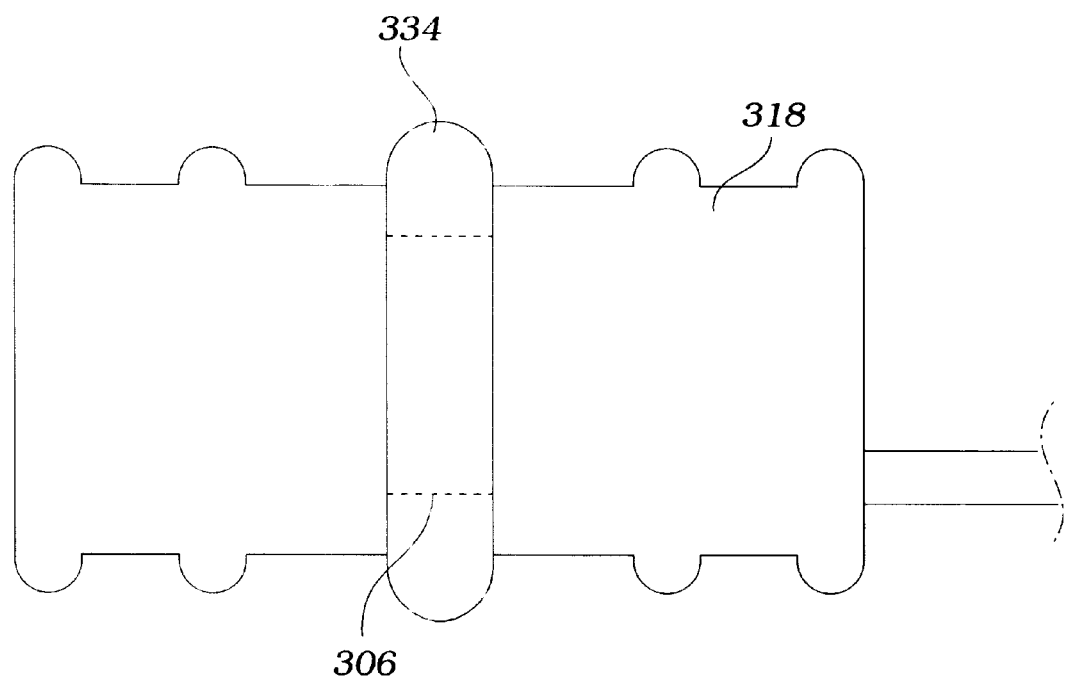
FIG. 18 illustrates the occluder of FIG. 16, having a deflated ring-shaped balloon.

In FIG. 17, fluid is injected to expand balloon 334, thereby constricting sleeve 318. As a result, blood flow is constricted. In FIG. 18, balloon deflation allows sleeve 318 to revert back to its pre-shaped geometry, increasing blood flow therethrough. Thus, balloon 334 can be inflated and deflated to vary the cross-sectional diameter of lumen 306 to vary flow rate.

Figure 19:
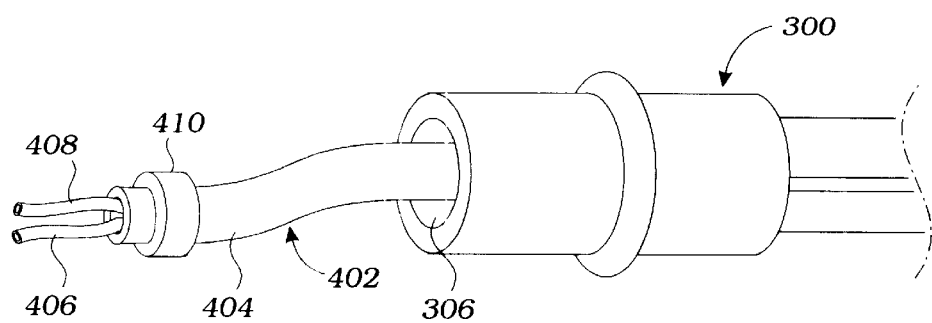
FIG. 19 illustrates a suction/atherectomy catheter introduced through the constrictor of FIG. 16.

The occlusion devices described herein can be employed with a variety of therapeutic catheters to treat vascular abnormalities. For example, as depicted in FIG. 19, suction/atherectomy catheter 402 can be inserted through lumen 306, such that the suction/atherectomy catheter is independently movable relative to occlusive device 300. Catheter 402 includes elongate tube 404 and distally located aspiration port 406, cutting device 408, and balloon 410 for removing thromboembolic material in a vessel.

Figure 20:
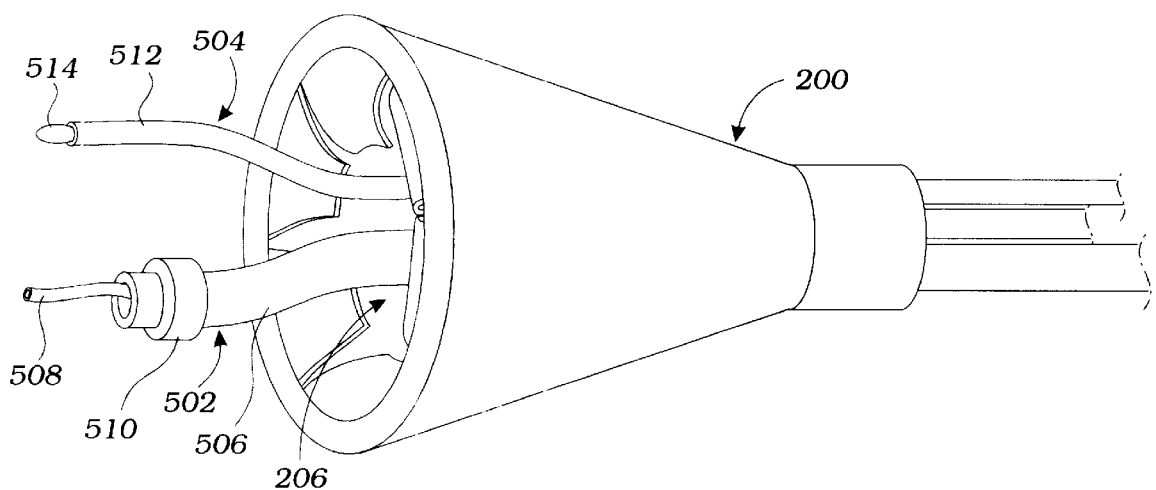
FIG. 20 illustrates a perfusion and an EPS catheter introduced through the constrictor of FIG. 16.

In FIG. 20, infusion catheter 502 and EPS catheter 504 are inserted through opening 206 of occlusion device 200, such that catheter 502 and 504 are independently movable relative to occlusion device 200. The infusion catheter, which includes elongate tube 506, distally located perfusion port 508, and expandable balloon 510, can be used to remove thromboembolic material in a vessel. EPS catheter 504, which includes elongate tube 512 and distally located ablation device 514, may be used to map out or ablate an extra conduction pathway in the myocardial tissue, e.g., in patients suffering from Wolff-Parkinson-White syndrome. The occlusion device, capable of augmenting cerebral perfusion, is therefore useful not only in facilitating definitive treatment but also in cerebral ischemia prevention during EPS and other cardiac interventions or cardiac surgery, such as coronary catheterization, where sudden fall in cerebral blood flow may occur due to arrhythmia, myocardial infarction, or congestive heart failure.

Figure 21A:
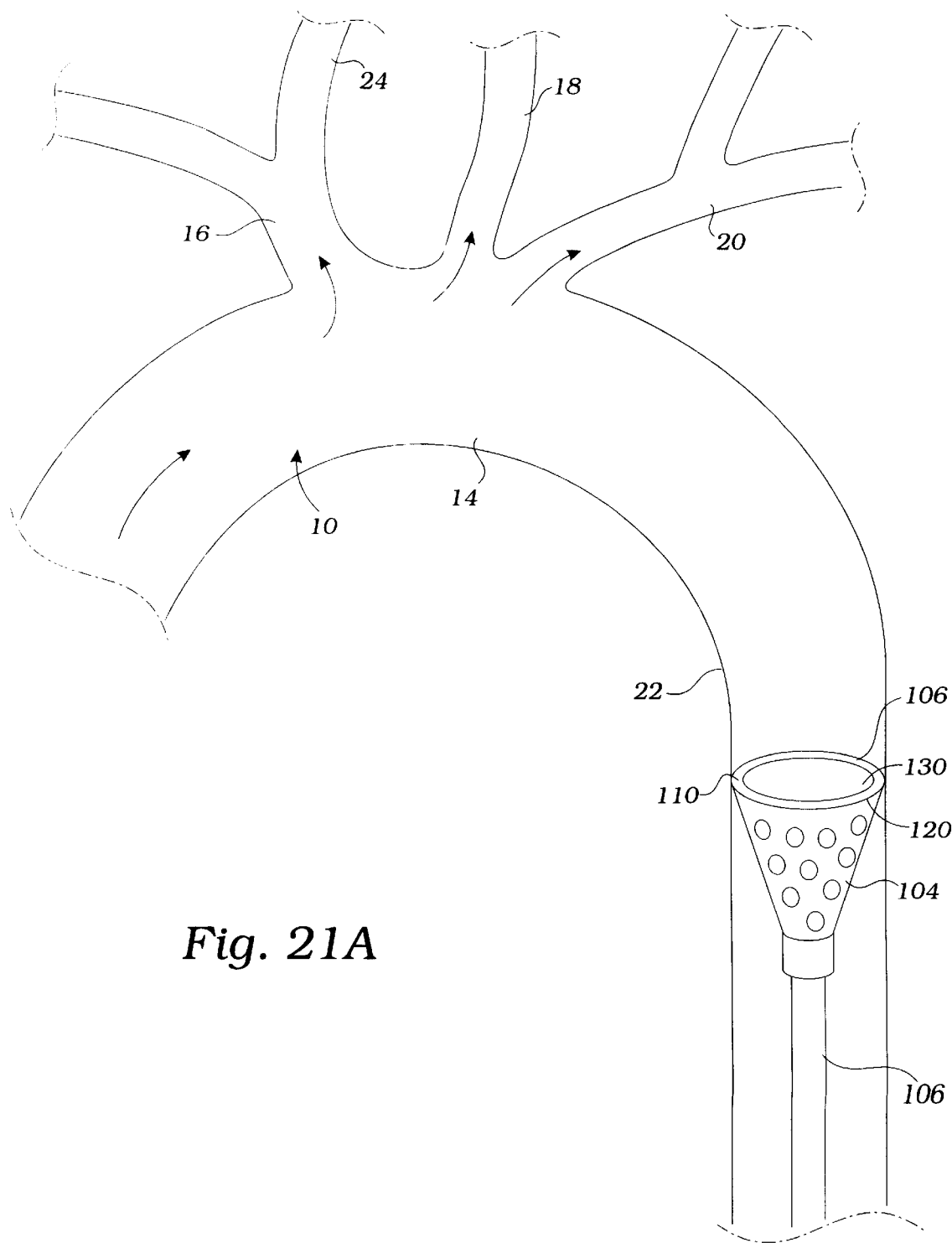
FIG. 21A illustrates the constrictor of FIG. 3 inserted in the aorta downstream from the left subclavian artery and partially occluding aortic blood flow.

Referring to FIG. 21A, occlusion device 100 described above can be used to partially occlude blood flow in aorta 10 of a patient suffering from global cerebral ischemia due to, e.g., septic shock, congestive heart failure, or cardiac arrest. Constrictor 104 can be introduced in its collapsed geometry through an incision on a peripheral artery, such as the femoral, subclavian, axillary, or radial artery, into the patient's aorta. A guide wire may first be introduced over a needle, and the collapsed constrictor is then passed over the guide wire and the needle to position distal to the takeoff of left subclavian artery 20 in the descending aorta. The constrictor is expanded, such that maximum periphery 110 of the occluder, formed by expandable ring 130, sealingly contacts the inner aortic wall. The position and orientation of the collapsed or expanded device can be checked by TEE, TTE, aortic arch cutaneous ultrasound in the emergency room, or IVUS and angiography in the angiogram suite.

The expanded constrictor is maintained during systole, during diastole, or during systole and diastole, during which blood distal to the brachiocephalic artery is forced to pass through opening 106, thereby providing a continuous partial occlusion of aortic blood flow. Alternatively, partial occlusion of aortic blood flow can be intermittent. As a result, blood flow to the descending aorta is partially diverted to brachiocephalic artery 16, left subclavian artery 20, and left carotid artery 18, thereby augmenting blood flow to the cerebral vasculature. In treating global ischemia, such as in shock, cerebral perfusion is increased by increasing blood flow through both carotid and vertebral arteries. Additionally, blood flow to the aorta is partially diverted to the coronary arteries by using the occlusion device, thereby augmenting flow to the coronary arteries. Using the partial occlusion methods during systemic circulatory failure may, therefore, improve cardiac performance and organ perfusion. By selectively increasing cerebral and coronary blood flow in this manner, the dosage of commonly used systemic vasoconstrictors, such as dopamine and norepinephrine, may be reduced or eliminated.

Figure 14:
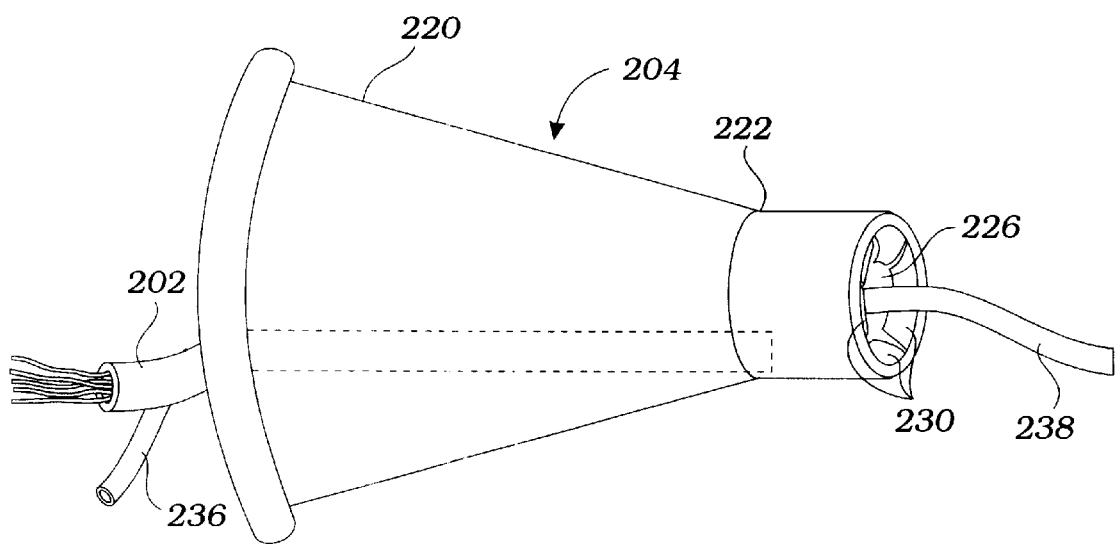
FIG. 14 illustrates another embodiment of the occluder having flaps included in the collar of the outer conical shell.
Figure 21B:
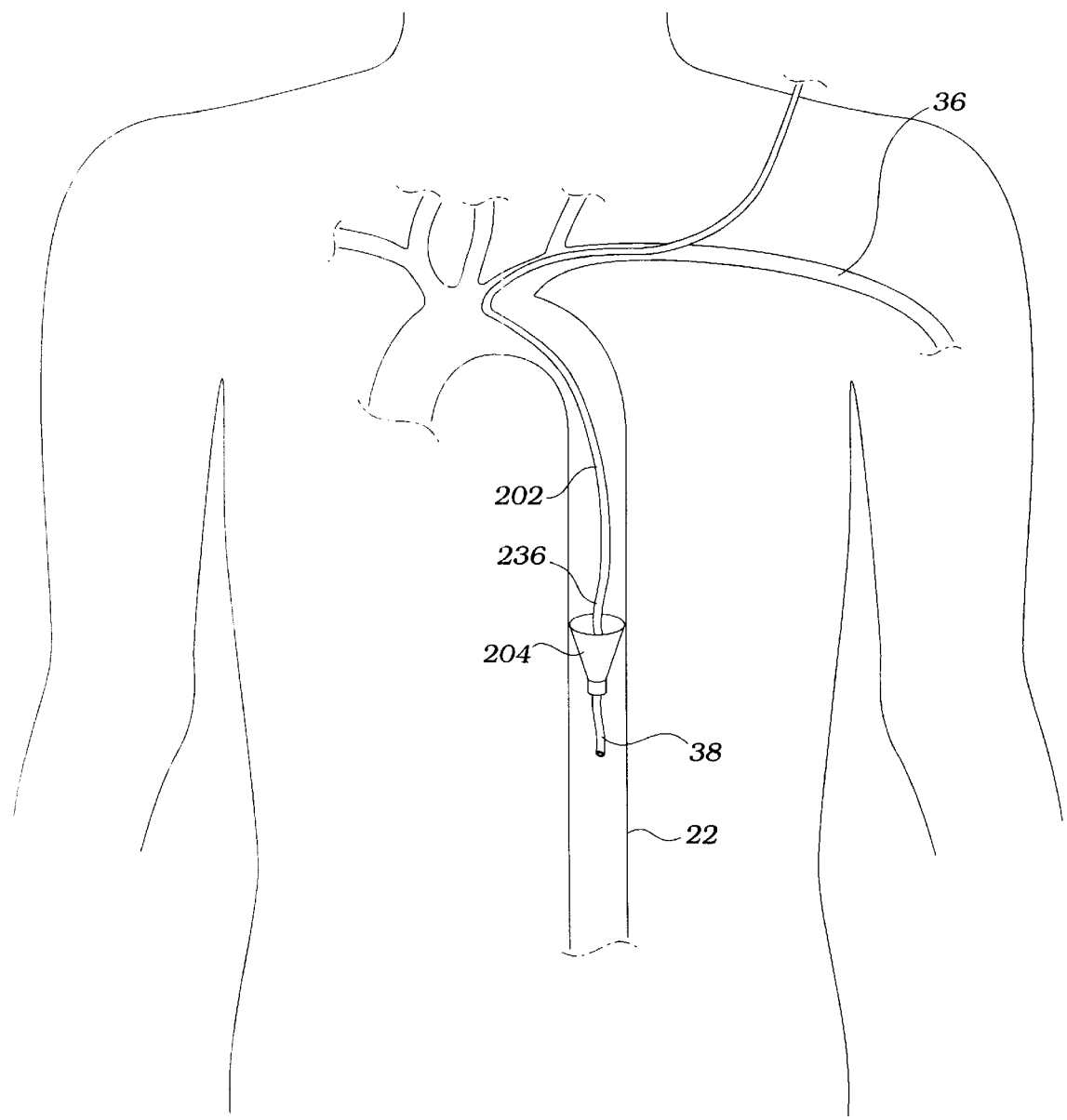
FIG. 21B illustrates the constrictor of FIG. 14 inserted in the aorta downstream from the left subclavian artery and partially occluding aortic blood flow.

Alternatively, the device of FIG. 14, much like the device used to extinguish the flame of a candle, can be introduced through an incision on left subclavian artery 36 as depicted in FIG. 21B. Constrictor 204 is inserted in aorta 22 distal to the takeoff of the left subclavian artery to provide partial, variable, and/or continuous aortic occlusion and is advanced antegrade into the descending aorta. This device is particularly useful in situations where peripheral incision can not be made on the femoral arteries due to arteriosclerosis, thrombosis, aneurysm, or stenosis.

The devices and methods described in FIGS. 21A and 21B are useful in treating stroke patients within few minutes of stroke symptom, and the treatment can be continued up to 96 hours or more. For example, in treating focal ischemia due to a thromboembolic occlusion in the right internal carotid artery the constrictor may be position distal to the takeoff of the left subclavian. As a result, blood flow is diverted to brachiocephalic artery 16 and left CCA to augment both ipsilateral and contralateral collateral circulation by reversing direction of flow across the Circle of Willis, i.e., increasing flow in the right external carotid artery and left common carotid artery. The collateral cerebral circulation is further described in details in co-pending U.S. application Ser. No. [Lyon & Lyon Docket No. 239/096], incorporated herein by reference.

Figure 22:
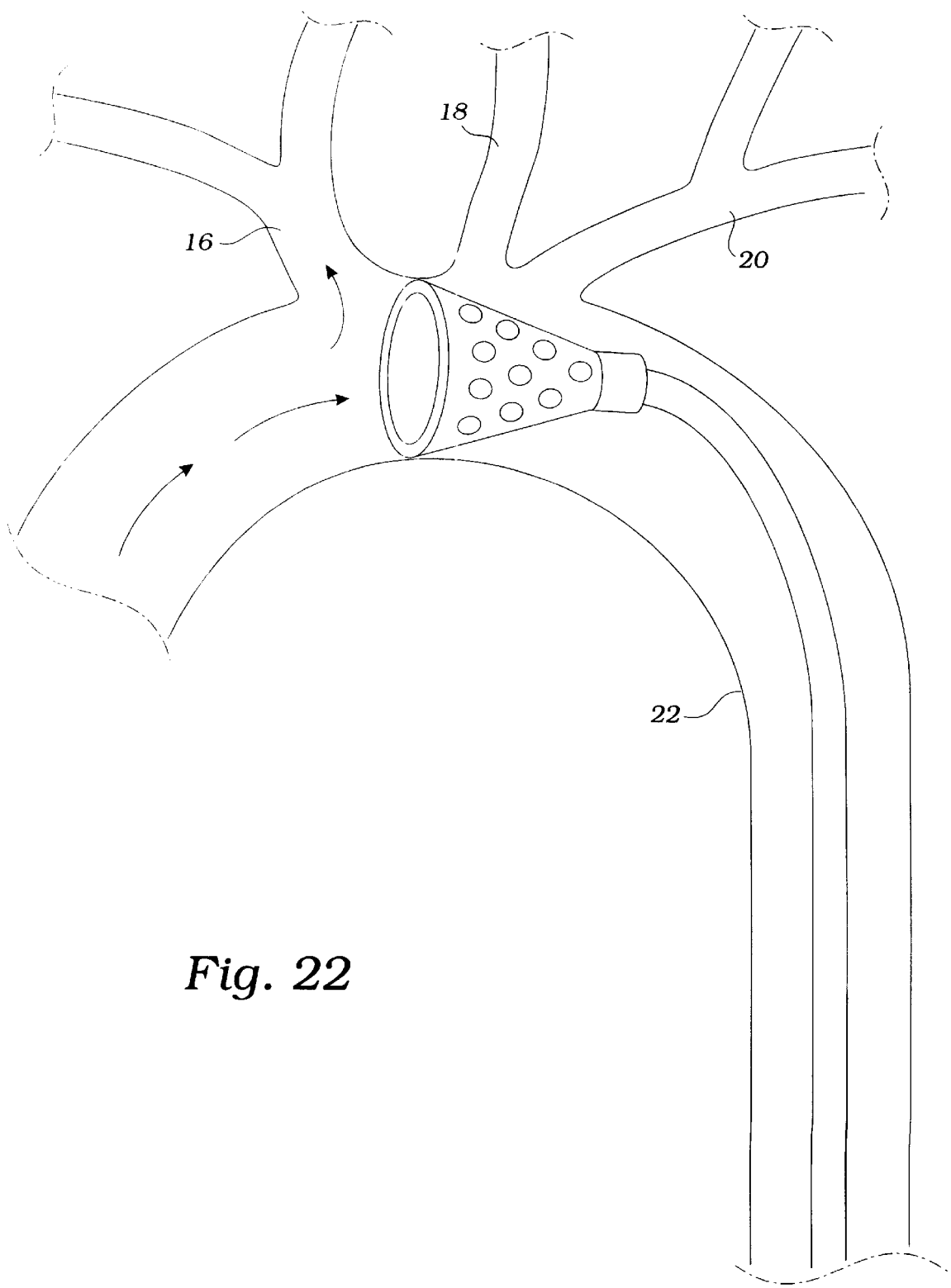
FIG. 22 illustrates the constrictor of FIG. 3 inserted in the aorta downstream from the right brachiocephalic artery and partially occluding aortic blood flow.

In treating focal ischemia due to a thromboembolic occlusion in the left internal carotid artery, for example, the constrictor can be positioned proximal to the takeoff of left carotid artery 18 and distal to the takeoff of brachiocephalic artery 16 as shown in FIG. 22. Contralateral collateral enhancement is provided by increasing flow through the brachiocephalic artery, thereby reversing blood flow in the right posterior communicating artery, right PCA, left posterior communicating artery 68 and anterior communicating artery, resulting in increased perfusion to the ischemic area distal to the occlusion and minimizing neurological deficits. Alternatively, the constrictor may be positioned distal to the takeoff of the left subclavian artery to provide both ipsilateral and contralateral collateral augmentation. Ipsilateral circulation is enhanced by increasing flow through the left external carotid artery and reversing flow along the left ophthalmic artery, both of which contribute to increased flow in the left ICA distal to the occlusion.

As a result of partially occluding aortic blood flow, blood pressure distal to the aortic occlusion may decrease, and this may result in a reduction in renal output. Blood pressure proximal the aortic occlusion will increase and may result in excessive rostral hypertension. The blood pressures, measured by the manometer, are monitored continuously, and based on this information the occlusion is adjusted to avoid peripheral organ damage. After resolution of the cerebral ischemia, the constrictor is collapsed and removed, thereby removing the aortic occlusion and restoring normal blood flow in the aorta.

Figure 23:
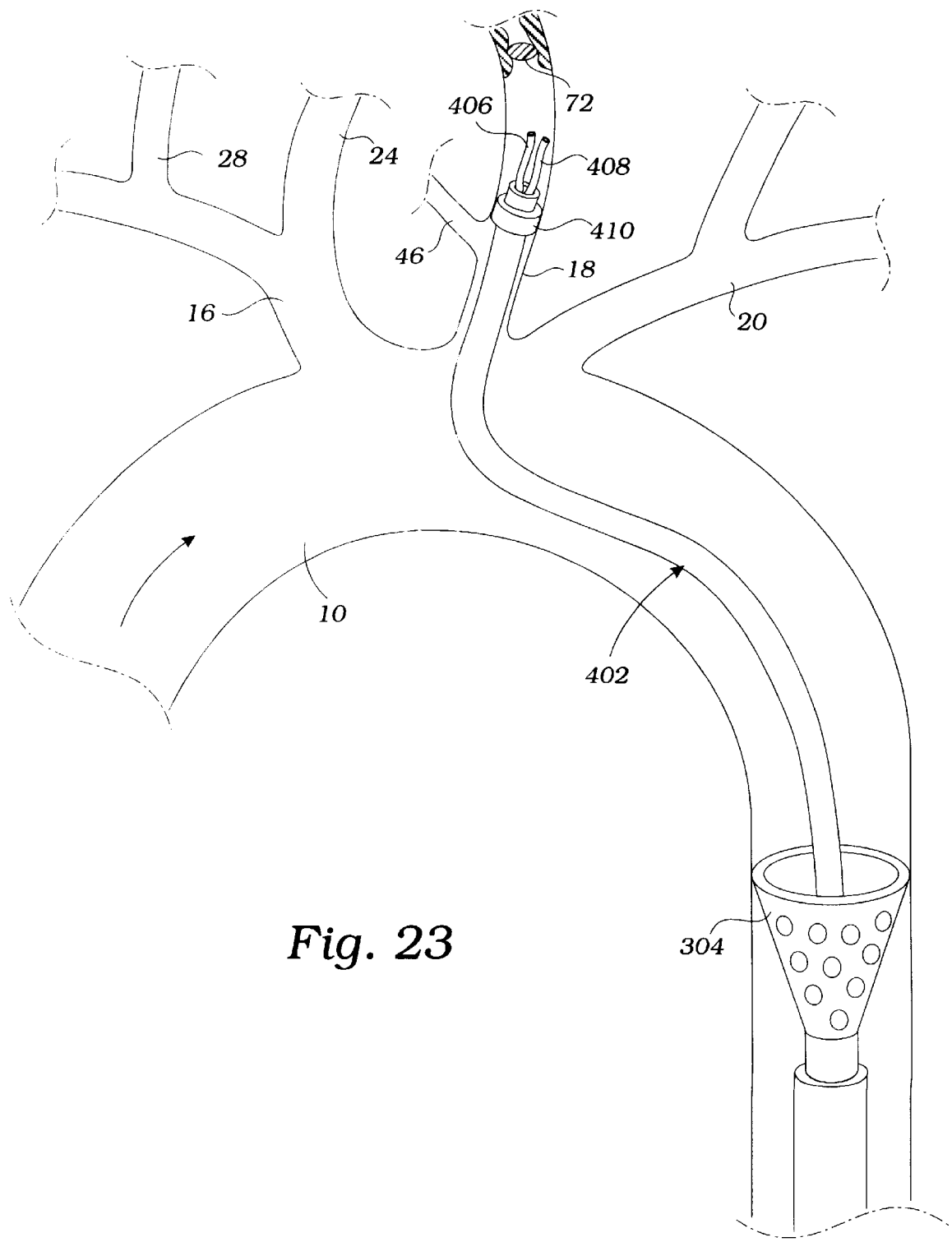
FIG. 23 illustrates a suction/atherectomy catheter introduced through the constrictor of FIG. 3 and inserted in the left carotid artery proximal to a thromboembolic occlusion.

In FIG. 23, constrictor 304 is inserted in aorta 10 and can be used to remove thromboembolic material 72 from left common carotid artery 18, while augmenting and maintaining cerebral perfusion distal to the occluding lesion. The occluder may be introduced through a guide sheath until it is positioned distal to left subclavian artery 20. In emergency situations, the constrictor can be inserted through a femoral incision in the emergency room, and atherectomy/suction catheter 402 can be inserted through the constrictor under angioscopic vision in the angiogram suite after the patient is stabilized hemodynamically. The atherectomy/suction catheter, which includes expandable balloon 410, distal aspiration port 406, and atherectomy device 408, is introduced through opening 306 until its distal end is positioned in left common carotid artery 18 proximal to the thromboembolic occlusion.

Constrictor 304 is then expanded to partially occlude aortic blood flow, thereby increasing perfusion to the ischemic region distal to the occluding lesion by enhancing ipsilateral collateral flow through left external carotid artery 46 and left vertebral artery 34 and contralateral collateral flow to right carotid artery 24 and right vertebral artery 28. The variable flow mechanism of constrictor 304 can be adjusted to control blood flow to the cerebral vasculature and the blood pressure. Balloon 410 of catheter 402 is expanded in the left common carotid artery, thereby creating a closed chamber between constrictor 410 and the thromboembolic occlusion. Suction can be applied to aspiration port 406 to create a negative pressure in the closed chamber, thereby increasing the pressure differential across the thromboembolic occlusion, which may dislodge the occluding lesion onto the aspiration port and remove the occluding lesion. Thromboembolic material 72 may be further removed by atherectomy device 408. The methods herein can also be used to remove thromboembolic occlusion in the vertebral artery. The occlusion device 304, therefore, not only augments cerebral perfusion in patients suffering from focal stroke or global ischemia, but also maintains cerebral perfusion while waiting for invasive or noninvasive intervention. The devices and methods of using atherectomy/suction catheter 102 are further described in copending U.S. application Ser. No. [Lyon & Lyon Docket No. 239/096], incorporated herein by reference.

Figure 24:
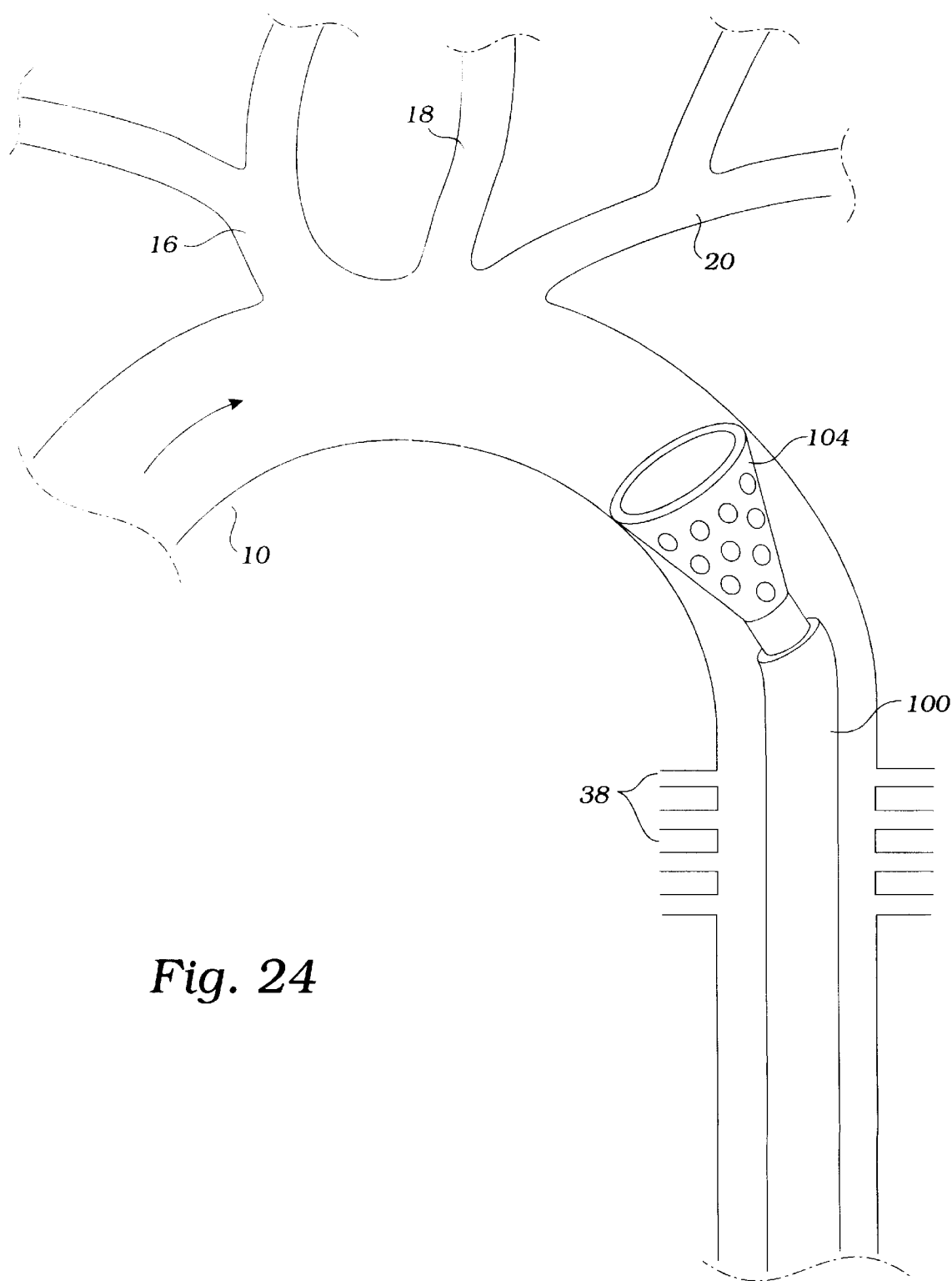
FIG. 24 illustrates the constrictor of FIG. 3 inserted in the aorta upstream from the lumbar or lumbar or spinal arteries.

During abdominal aortic aneurysm (AAA) surgery, lumbar or spinal arteries, which provide blood supply to the spinal cord, are often dissected away from the diseased abdominal aorta, resulting in reduction of blood flow to the spinal cord. The devices herein disclosed may be used to condition the spinal cord prior to AAA repair, thereby reducing the damage resulting from spinal ischemia during surgery. In FIG. 24, constrictor 104 is inserted in aorta 10 and expanded preferably distal to left subclavian artery 20 and proximal to lumbar arteries 38. As a result, blood flow to the lumbar or spinal arteries is reduced. When this device is used in patients anticipating a major thoracoabdominal surgery, such as AAA repair, approximately 24 hours prior to surgery, blood flow to the lumbar arteries can be intentionally reduced to induce mild spinal ischemia, thereby conditioning the spinal cord to produce neuroprotective agents which may protect the spinal cord from more significant ischemic insult during surgery.

Figure 25:
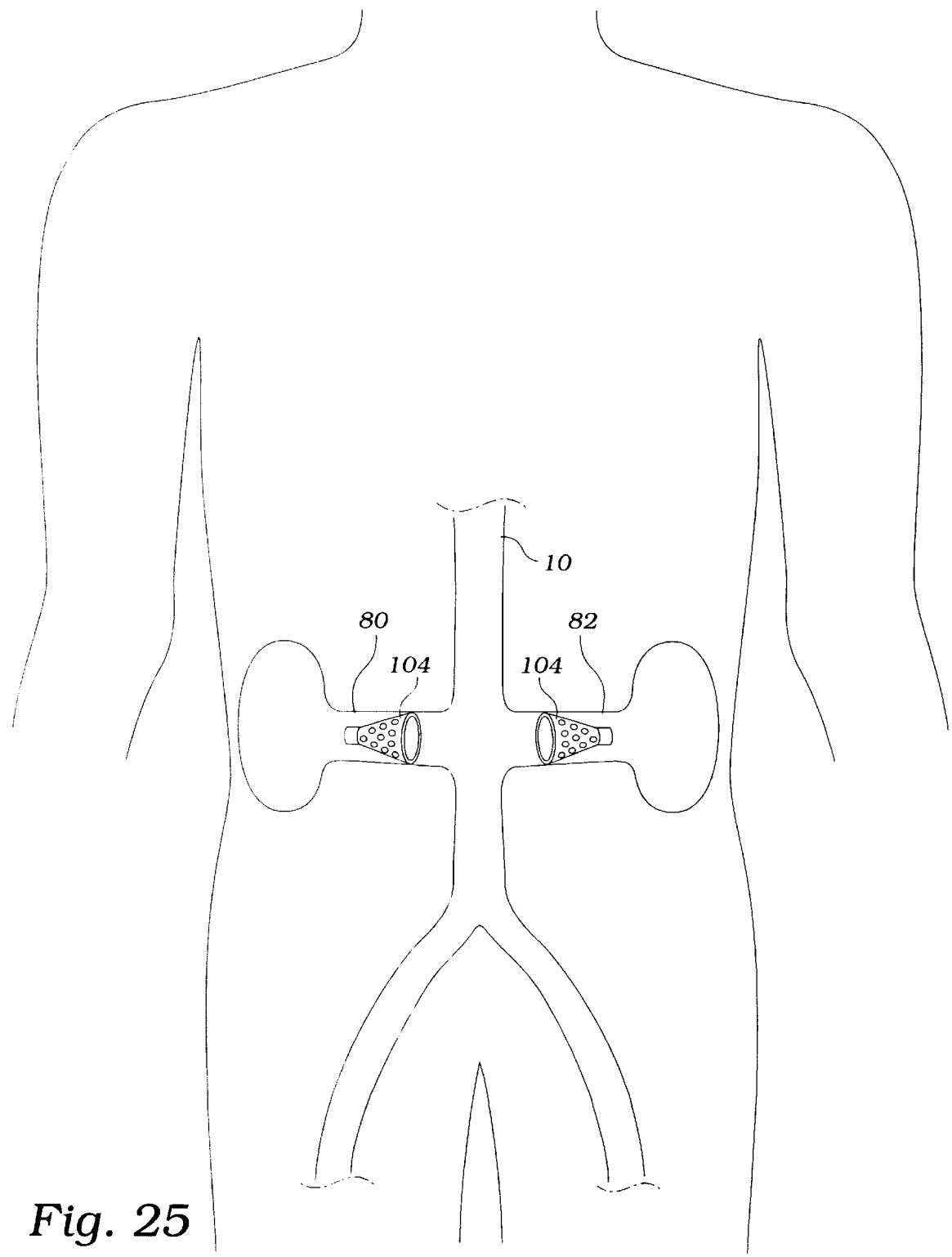
FIG. 25 illustrates the constrictor of FIG. 3 inserted in the renal arteries.

In hypertension, end organ damage often results, e.g., cardiac, renal, and cerebral ischemia and infarction. The devices and methods herein may be employed in hypertension to protect the kidneys from ischemic insult. In FIG. 25, constrictors 104, which can be introduced through a femoral artery, are inserted in right renal artery 80 and left renal artery 82. The constrictors are expanded to partially occlude blood flow from descending aorta 10 to the renal arteries, thereby reducing blood pressure distal to the occlusion. The constrictors can be deployed for the duration of any systemic hypertensive condition, thereby protecting the kidneys from damage that might otherwise be caused by the hypertension.

The length of the catheter will generally be between 20 to 150 centimeters, preferably approximately between 30 and 100 centimeters. The inner diameter of the catheter will generally be between 0.2 and 0.6 centimeters, preferably approximately 0.4 centimeters. The diameter of the base of the outer conical shell will generally be between 0.3 and 3.0 centimeters, preferably approximately 0.5 and 2.0 centimeters. The diameter of the inflated balloon occluder will generally be between 0.3 and 3.0 centimeters, preferably approximately 0.5 and 2.0 centimeters. The ports of the inner and outer conical shells will generally have a diameter of between 1 to 6 millimeters, preferably approximately 3 to 4 millimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A medical device for partial aortic occlusion for cerebral perfusion augmentation, comprising:

an elongate member having proximal and distal ends, the distal end adapted for insertion through the femoral artery into the descending aorta;

an expandable constrictor mounted at the distal end of the elongate member, the constrictor expandable to engage the lumen of the aorta and having one or more passages adjustable independently of the expansion of the constrictor through which distal blood flow may be carried; and a catheter extending through the constrictor and independently operable to access the carotid arteries, the coronary arteries, the aortic wall, and the conducting tissue of the heart and myocardium, the catheter carrying a medical device.

2. The device of claim 1, further comprising a manometer mounted distal the expandable constrictor for measuring blood pressure in the proximal aorta.

3. The device of claim 1, further comprising a variable flow mechanism in operative association with the adjustable passages for controlling blood flow through the passages.

4. The device of claim 1, wherein the catheter includes aspiration capabilities.

5. The device of claim 1, wherein the medical device is an atherectomy catheter.

6. The device of claim 1, wherein the medical device is an infusion catheter.

7. The device of claim 1, wherein the medical device is an EPS catheter.

8. A medical device for partial aortic occlusion for cerebral perfusion augmentation, comprising:

an elongate member having proximal and distal ends, the distal end adapted for insertion through the femoral artery into the descending aorta;

an expandable constrictor mounted at the distal end of the elongate member, the constrictor expandable to engage the lumen of the aorta and having one or more passages adjustable independently of the expansion of the constrictor through which distal blood flow may be carried;

a manometer mounted distal the expandable constrictor for measuring blood pressure in the proximal aorta; and a catheter extending through the constrictor and independently operable to access the carotid arteries, the coronary arteries, the aortic wall, and the conducting tissue of the heart and myocardium, the catheter carrying a medical device.

9. The device of claim 8, further comprising a variable flow mechanism in operative association with the adjustable passages for controlling blood flow through the passages.

10. The device of claim 8, wherein the catheter includes aspiration capabilities.

11. The device of claim 8, wherein the medical device is an atherectomy catheter.

12. The device of claim 8, wherein the medical device is an infusion catheter.

13. The device of claim 8, wherein the medical device is an EPS catheter.

* * * * *